US 11,351,134 B2

(12) United States Patent
James-Meyer et al.

(10) Patent No.: US 11,351,134 B2
(45) Date of Patent: Jun. 7, 2022

(54) SMALL MOLECULE AGENTS, COMPOSITIONS, AND FORMULATIONS, FOR INTERNAL USE, DISPLAYING INHIBITORY ACTIVITY AGAINST GRAM-POSITIVE AND/OR GRAM-NEGATIVE ORGANISMS

(71) Applicant: NATUREZA, INC., Denison, TX (US)

(72) Inventors: Lynn S. James-Meyer, Denison, TX (US); Gerald C. Coles, Bristol (GB); Tristan Alexander Cogan, Weston-Super-Mare (GB)

(73) Assignee: Natureza Products, Inc., Denison, TX (US)

( * ) Notice: Subject to any disclaimer, the term of this patent is extended or adjusted under 35 U.S.C. 154(b) by 0 days.

(21) Appl. No.: 16/102,684

(22) Filed: Aug. 13, 2018

(65) Prior Publication Data
US 2019/0046483 A1 Feb. 14, 2019

Related U.S. Application Data

(60) Provisional application No. 62/681,087, filed on Jun. 5, 2018, provisional application No. 62/569,284, filed on Oct. 6, 2017, provisional application No. 62/544,755, filed on Aug. 11, 2017.

(51) Int. Cl.
| | |
|---|---|
| *A61K 31/197* | (2006.01) |
| *A61P 31/04* | (2006.01) |
| *A61K 9/14* | (2006.01) |
| *A61K 31/23* | (2006.01) |
| *A61K 31/7024* | (2006.01) |
| *A61K 47/24* | (2006.01) |
| *A61K 47/36* | (2006.01) |
| *A61K 9/19* | (2006.01) |
| *A61K 9/10* | (2006.01) |

(52) U.S. Cl.
CPC .............. *A61K 31/197* (2013.01); *A61K 9/10* (2013.01); *A61K 9/145* (2013.01); *A61K 9/146* (2013.01); *A61K 9/19* (2013.01); *A61K 31/23* (2013.01); *A61K 31/7024* (2013.01); *A61K 47/24* (2013.01); *A61K 47/36* (2013.01); *A61P 31/04* (2018.01)

(58) Field of Classification Search
CPC .... A61K 31/197; A61K 31/23; A61K 31/722; A61K 31/7024; A61P 31/04; A61P 9/127
See application file for complete search history.

(56) References Cited

U.S. PATENT DOCUMENTS

| | | | |
|---|---|---|---|
| 6,204,230 B1 | 3/2001 | Taylor et al. | |
| 6,716,970 B2 * | 4/2004 | Hung | A61L 12/14 536/124 |
| 7,846,895 B2 | 12/2010 | Eckert et al. | |
| 2008/0262084 A1 | 10/2008 | Daftary et al. | |
| 2011/0237686 A1 | 9/2011 | Ng et al. | |
| 2012/0178731 A1 | 7/2012 | Guthery | |
| 2013/0289005 A1 | 10/2013 | Guthery | |
| 2014/0051650 A1 | 2/2014 | Ardolino et al. | |
| 2015/0157591 A1 | 6/2015 | Zhu et al. | |
| 2016/0175244 A1 | 6/2016 | Schlievert | |
| 2016/0303148 A1 | 10/2016 | Kozono et al. | |

FOREIGN PATENT DOCUMENTS

| | | |
|---|---|---|
| JP | 01197431 A | 9/1989 |
| JP | H04-5489 B * | 1/1992 |
| WO | WO 2007/031519 | 3/2007 |
| WO | WO 2008/062428 | 5/2008 |

(Continued)

OTHER PUBLICATIONS

Kabara, J. et al., Antimicrobial Agents and Chemotherapy, "Relationship of Chemical Structure and Antimicrobial Activity of Alkyl Amides and Amines", 1972, vol. 2, No. 6, pp. 492-498 (Year: 1972).*

Shapiro, S., Oral Microbiology and Immunology, "The inhibitory action of fatty acids on oral bacteria", 1996, vol. 5, pp. 350-355 (Year: 1996).*

Komazaki et al., machine translation of H04-005489 (published Jan. 1992) after examination (also published as S59-139310, Aug. 1984) (Year: 1992).*

Korupalli, C. et al., Biomaterials, "Acidity-triggered charge-convertible nanoparticles that can cause bacterium-specific aggregation in situ to enhance photothermal ablation of focal infection", 2017, (published online Nov. 2016), vol. 116, pp. 1-9 (Year: 2017).*

Sigma Aldrich, "glycol chitosan", CAS No. 123938-86-3, obtained from online catalog Feb. 25, 2021, available at https://www.sigmaaldrich.com/catalog/product/sigma/g7753?lang=en&region=US# (Year: 2021).*

(Continued)

*Primary Examiner* — Bahar Craigo
(74) *Attorney, Agent, or Firm* — Monique A. Vander Molen

(57) ABSTRACT

Active components comprising lauric acid, or a lauric acid derivative, are utilized independently, or in combination, to provide new and useful compositions for bacteriostatic action against susceptible pathogens. The lauric acid derivative includes one or more of 12-aminododecanoic acid, 12-amino-1-dodecanoic acid methyl ester, sucrose monolaurate, 12-(7-nitrobenzofurazan-4-ylamino) dodecanoic acid, 4-nitrophenyl dodecanoate, 1-lauroyl-rac-glycerol, 3-oxo-N-(2-oxocyclohexyl) dodecanamide, butyl laurate, benzyl laurate, isoamyl laurate, monolaurin, isopropyl laurate, pentyl laurate, and hexyl laurate. A preparation includes combining the active component with lecithin, and after an initial processing phase, coating with chitosan or a carrier. Final compositions may be or may contain particles, such as nanoparticles. Final compositions, or formulations containing said final compositions, may be utilized internally, causing one or more membrane changes (e.g., a membrane of an internal target pathogen, which may or may not be an antibiotic-resistant pathogen). At least some compositions inhibit growth of one or more Gram-positive bacterial species and one or more Gram-negative bacterial species.

20 Claims, 2 Drawing Sheets

(56) References Cited

FOREIGN PATENT DOCUMENTS

| WO | WO 2008/137917 | 11/2008 |
| WO | WO 2016/061561 | 4/2016 |

OTHER PUBLICATIONS

Yan, L. et al., Small, "ApH-Responsive Drug-Delivery Platform Based on Glycol Chitosan-Coated Liposomes", 2015, vol. 11, No. 37, pp. 4870-4874 (Year: 2015).*

EPO Form 1507S, European Patent Office Communication for extended European Search Report, for EP Application No. 15850205.4, dated Mar. 28, 2018 (1 page).

Supplementary European Search Report and Annex to the European Search Report and Information on Search Strategy, and Examination via EPO Form 1703, for EP Application No. 15850205.4, dated Mar. 28, 2018 (6 pages).

Zhang, H., et al., "Quantitative structure-activity relationships of antimicrobial fatty acids and derivatives against *Staphylococcus aureus*," J. Zhejiang Univ-Sci B (Biomed & Biotechnol) 2012 vol. 13(2):83-93.

Kabara, et al., Fatty acids and derivatives as antimicrobial agents, Antimicrobial Agents Chemother., 1972, vol. 2(1), pp. 23-28.

Notification of Transmittal of the International Search Report and the Written Opinion of the International Searching Authority, with the International Search Report and Written Opinion of the International Searching Authority, for International Application No. PCT/US2018/046576, dated Oct. 24, 2018, 9 pages.

Hattori, et al., Effects of long-chain fatty acids and fatty alcohols on the growth of *Streptococcus mutans*, Chem. Pharm. Bull., 1987, vol. 35(8), pp. 3507-3510.

Sun, et al., Antibacterial actions of fatty acids and monoglycertids against Helicobacter pylori, FEMS Immunology Medical Microbiol., 2003, vol. 36, pp. 9-17.

Tomarelli, et al. The effect of fatty acids on the growth of strains of Lactobacillus bifidus, JBC, 1950, vol. 187, pp. 197-204.

Yang D., et al., The antimicrobial activity of liposomal lauric acids against *Propionibacterium acnes*, Biomaterials, Aug. 8, 2009 (online), vol. 30, pp. 6035-6040.

Notification of Transmittal of the International Search Report and the Written Opinion of the International Searching Authority, with the International Search Report and Written Opinion of the International Searching Authority, for International Application No. PCT/US2015/56111, dated Jan. 7, 2016, 11 pages.

Notification Concerning Transmittal of International Preliminary Report on Patentability, with International Preliminary Report on Patentability, for International Application No. PCT/US2015/56111, dated Apr. 27, 2017, 8 pages.

Kato S., et al., Effect of pH on the antimicrobial action of sucrose laurate, Food Hygiene and Safety Science, Jun. 1986, vol. 27, issue 3, pp. 218-223.

Zhang X., et al., Comparative study of surface-active properties and antimicrobial activities of disaccharide monsters, PLoS ONE, Dec. 22, 2014, 9(12):e114845, DOI:10.1371/journal.pone.0114845, pp. 1-19.

"Lecithin" descriptions, Science Direct, available at https://www.sciencedirect.com/topics/chemistry/lecithin, downloaded Feb. 24, 2020.

EP Communication and Supplementary European Search Report for EP 18843511.9, dated Dec. 9, 2020, European Patent Office, Munich, Germany, (13 pages).

Sunamoto, J., et al., JP 01197431 translation published Aug. 9, 1989 (2 pgs.).

* cited by examiner

SMALL MOLECULE AGENTS, COMPOSITIONS, AND FORMULATIONS, FOR INTERNAL USE, DISPLAYING INHIBITORY ACTIVITY AGAINST GRAM-POSITIVE AND/OR GRAM-NEGATIVE ORGANISMS

CROSS REFERENCE TO RELATED APPLICATIONS

This patent application claims the benefit of priority to U.S. Provisional Appl. No. 62/544,755 filed Aug. 11, 2017, and U.S. Provisional Appl. No. 62/569,284 filed Oct. 6, 2017, and U.S. Provisional Appl. No. 62/681,087 filed Jun. 5, 2018, each prior filed provisional patent application being incorporated herein by reference in its entirety, and to the maximum extent.

BACKGROUND

There remains a need for new and improved active components, one or more of which may be harnessed, as a direct acting, small molecule agent having antimicrobial properties, said one or more active components being utilized and/or harnessed individually, independently, or in a suitable combination.

There remains a need for one or more active components, as described above, that may be harnessed, as a direct acting, small molecule agent having antimicrobial properties, said one or more active components being utilized and/or harnessed individually, independently, or in a suitable combination, and when so utilized and/or harnessed as at least one direct acting, small molecule agent, said at least one direct acting, small molecule agent is a new and/or improved small molecule agent with a good safety profile.

There remains a need for one or more active components, as described above, that may be harnessed, as a direct acting, small molecule agent having antimicrobial properties, said one or more active components being utilized and/or harnessed individually, independently, or in a suitable combination, and when so utilized and/or harnessed as at least one direct acting, small molecule agent, said one or more active components and/or said at least one direct acting is new and/or improved, having a good safety profile, and a status and/or notification as Generally Recognized As Safe (GRAS) (e.g., in compliance with or in association with U.S. Food and Drug Administration).

There remains a need for one or more active components as described above that may be harnessed as a direct acting, small molecule agent having antimicrobial properties and suitable for utilization against one or more harmful and/or infectious pathogens, in which said one or more active components may be utilized and/or harnessed individually, independently, or in a suitable combination.

There remains a need for one or more active components as described above that may be harnessed as at least one direct acting, small molecule agent having antimicrobial properties and suitable for utilization against one or more harmful and/or infectious pathogens, including one or more antibiotic-resistant pathogens, in which said one or more active components may be utilized and/or harnessed individually, independently, or in a suitable combination.

There remains a need for one or more active components as described above that may be harnessed as at least one direct acting, small molecule agent having antimicrobial properties and suitable against one or more antibiotic-resistant pathogens, in which said one or more active ingredients may be utilized and/or harnessed individually, independently, or in a suitable combination, and, when so utilized and/or harnessed as the at least one direct acting, small molecule agent, has a good safety profile.

There remains a need for one or more active components as described above that may be harnessed as at least one direct acting, small molecule agent having antimicrobial properties and suitable against one or more antibiotic resistant pathogens, in which said one or more active components may be utilized and/or harnessed individually, independently, or in a suitable combination, and, when so utilized and/or harnessed as the at least one direct acting, small molecule agent, has a good safety profile and a status and/or notification as GRAS.

There remains a need for one or more active components as described above that may be harnessed as at least one direct acting, small molecule agent having antimicrobial properties, suitable against one or more antibiotic resistant pathogens, and effective against one or more antibiotic resistant pathogens identified in a World Health Organization (WHO) Global Priority List. See, WHO, Global priority list of antibiotic-resistant bacteria to guide research, discovery, and development of new antibiotics, Feb. 27, 2017, 7 pages. The Global Priority List includes the following pathogens: *Acinetobacter baumannii* (carbapenem-resistant strains), *Pseudomonas aeruginosa* (carbapenem-resistant strains), Enterobacteriaceae (carbapenem-resistant strains, third generation cephalosporin-resistant strains, such as *Klebsiella pneumonia, Escherichia coli, Enterobacter* spp., *Serratia* spp. *Proteus* spp., *Providencia* spp., *Morganella* spp.), *Mycobacterium* spp., *Enterococcus faecium* (vancomycin-resistant strains), *Staphylococcus aureus* (methicillin-resistant strains, vancomycin intermediate and resistant strains), *Helicobacter pylori* (clarithromycin-resistant strains), *Campylobacter* (fluoroquinolone-resistant strains), *Salmonella* spp. (fluoroquinolone-resistant strains), *Neisseria gonorrhoeae* (third generation cephalosporin-resistant strains, fluoroquinolone resistant strains), *Streptococcus pneumoniae* (penicillin-non-susceptible strains), *Haemophilus influenza* (ampicillin-resistant strains), *Shigella* spp. (fluoroquinolone-resistant strains). Said one or more active components may be utilized and/or harnessed individually, independently, or in a suitable combination.

There remains a need for one or more active components as described above that may be harnessed as at least one direct acting, small molecule agent having antimicrobial properties, suitable against more than one antibiotic resistant pathogen, and effective against more than one antibiotic resistant pathogen identified by the WHO Global Priority List, in which said one or more active components may be utilized and/or harnessed individually, independently, or in a suitable combination.

There remains a need for one or more active components that may be harnessed as a direct acting, small molecule agent having antimicrobial properties, suitable against a plurality of antibiotic resistant pathogens, and effective against a plurality of and/or more than half of the antibiotic-resistant pathogens identified by the WHO Global Priority List, in which said one or more active components may be utilized and/or harnessed individually, independently, or in a suitable combination.

There is also a need for at least one new and/or improved direct acting, small molecule agent with antimicrobial properties, suitable for utilization against one or more pathogens.

There is also a need for at least one new and/or improved direct acting, small molecule agent with antimicrobial properties, suitable for utilization against one or more pathogens, including harmful and/or infectious pathogens, and/or antibiotic-resistant pathogens.

There is still further a need for at least one new and/or improved direct acting, small molecule agents with antimicrobial properties, suitable for utilization against one or more antibiotic-resistant bacteria, and effective against one or more antibiotic-resistant pathogens identified by the WHO Global Priority List.

There is even further a remaining need for at least one new and/or improved direct acting, small molecule agents with antimicrobial properties, suitable for utilization against a plurality of antibiotic-resistant bacteria, and effective against a plurality of and/or more than half of the antibiotic-resistant pathogens identified by the WHO Global Priority List.

When so utilized and/or harnessed as the at least one direct acting, small molecule agent, as described above, a good safety profile and/or a status and/or notification as GRAS may also be needed.

Medium chain fatty acids with seven to 12 carbon atoms, such as lauric acid with 12 carbon atoms, have been found to have health benefits. Moreover, the medium chain fatty acid, lauric acid, has been found to exhibit some selective bacteriostatic activity, having generally a weak inhibitory activity when applied at low amounts topically, or when added at low amounts to certain foods, or when evaluated in vitro at low amounts in growth cultures, the selective activity being against certain gram-positive microorganisms, such as gram-positive organisms, *Streptococcus* group A and *Streptococcus* beta-hemolytic non-A, and *S. aureus*, as well as *Candida*. The in vitro minimal inhibitory concentration (MIC, or lowest concentration of compound at which no microscopic evidence of growth, as turbidity, was observed as compared with control samples) of lauric acid against such gram-positive organisms is such that it is considered acceptable for use in topical formulations for bacteriostatic purposes. When provided in higher concentrations (e.g., two parts lauric acid to one part diluent), lauric acid, applied topically, may be associated with bactericidal activity; however, there have also been reports of a high level of resistance associated with such topical applications of lauric acid, such as in microorganisms that are native in the flora of the skin (e.g., enterococci, lactic acid bacteria, staphylococci). With topical application of lauric acid, bactericidal activity also appears to be selective, being stronger against certain gram-positive microorganisms, such as *streptococcus* species, as compared with *S. aureus*, and generally ineffective against many common gram-negative bacteria (e.g., *E. coli*). In some topical or in vitro studies, a fatty acid, such as lauric acid, has been found to be less potent at physiologic pH values.

According to several reports, the free carboxyl group in a medium chain fatty acid, such as lauric acid, appears necessary for activity against gram-positive microorganisms. For example, esterification of the free carboxyl group on a medium chain fatty acid, such as lauric acid, has been found to greatly decrease bactericidal activity. When esterified (e.g., with a monohydric alcohol, such as cholesterol, methanol, ethanol), there has been found to be a great reduction in overall inhibitory effect or bacteriostatic activity against the same gram-positive bacteria. In some reports, lauric acid esterified with monohydric alcohols, cholesterol, and methanol, no longer demonstrated any bacterial inhibition when tested in vitro against the above gram-positive organisms. For example, with an ethyl group, there is no activity in some reports; ethyl laurate appears to be inactive. With a methyl group, there is very little activity, and sometimes no activity; methyl laurate appears to be similarly ineffective. According to other reports, fatty acid derivatives (aldehydes, acetate, ethyl ester, amide or substituted amide), while somewhat active (e.g., offering some but mimimal activity against certain bacteria), have demonstrated far less activity than their corresponding acids. Some lacto-bacteria were found to be protected against lauric acid toxicity when one or more emulsifying agents were introduced with the fatty acid (e.g., Tween 80, Tween 60, phosphatide, lipositol). Additional protection of such bacteria against the inhibitory activity of lauric acid was also demonstrated with addition of a protein (e.g., bovine serum albumin) or dialyzed whey. Thus, the literature has been conflicted, and does not indicate any real benefit in the use of a medium chain fatty acid, such as lauric acid, in the forms described above.

When lauric acid is esterified to a polyhydric alcohol (such as glycerol), the esterified complex may be more active (e.g., against at least some of the selective gram-positive organisms). For this reason, it has been contemplated by many investigators that improving activity is associated with esterification to a glycerol, the improvement being a mono-ester (also known as monolaurin). Interestingly, the higher activity of monolaurin (via the esterification to a monoglycerin) is decreased and/or inactivated in the presence of certain additives, such as a starch and certain phospholipids. The number of inconsistencies as well as contradictory reports over the years regarding bacteriostatic and/or bactericidal activity of fatty acids, including medium chain fatty acids, such as lauric acid, and certain derivatives thereof, as represented above, is likely connected to its inability to be utilized internally.

What raises more issues when trying to utilize a medium chain fatty acid, such as lauric acid, as an anti-infective agent is its insolubility. Due to its insolubility, and other physio-chemical properties, a medium chain fatty acid, such as lauric acid, has generally been contemplated in its fatty form only for topical use against only the certain gram-positive bacteria described above, provided in high concentrations, or, has been added in its fatty form to certain packaged foods for use against only the certain gram-positive bacteria described above, provided in high concentrations, to improve food shelf-life of the food while in the packaged state (e.g., to assist with inhibition of pathogen growth only before the food is opened and eaten). In fact, a fatty acid, such as lauric acid has not been found to be effective when taken internally. When ingested, it is quickly converted and/or is quickly broken down, and, as a result, does not remain in a form associated with its inhibitory activity with topical or packaged uses (as described above). While, some have found some weak activity of certain fatty acids, the weak activity does not translate to prevention of growth of the pathogen.

The plethora of studies with lauric acid, and certain derivatives (exemplified above), has, so far, not led to fruition, particularly in pursuit of a direct acting, small molecule agent having fitting antimicrobial properties directed against gram-positive and/or gram-negative pathogens (e.g., harmful, toxigenic, or infectious gram-positive and/or gram-negative organisms, rather than native bacteria or normal microflora) that reside inside or within a subject.

When ingested, a medium chain fatty acid, such as lauric acid, is metabolized differently from many other fatty acids, as the medium chain fatty acids generally move directly to the liver from the digestive tract where they are broken down as a quick source of energy, or turned into a ketone. This, and the general insolubility of a medium chain fatty acid, such as lauric acid, has continued to provide challenges. To date, a medium chain fatty acid, such as lauric acid, is not readily suitable to be internalized or ingested while also providing, after internalization or ingestion, direct-acting and fitting antimicrobial properties against internal and harmful and/or infectious pathogens. Thus, to date, there remains a dearth of suitable compositions as direct acting, small molecule agents having fitting antimicrobial properties directed against Gram-positive and/or Gram-negative pathogens (e.g., harmful and/or infectious Gram-positive and/or Gram-negative organisms) that reside inside or within a subject, in which the direct-acting, small molecule agents comprise at least one or more active components having a medium chain fatty acid backbone, or a 12-carbon atom backbone.

SUMMARY

Described herein are previously unreported compositions and/or new uses of said compositions that meet at least one or more than one of the needs described above. Said compositions overcome one or more of the issues described above. Such compositions, many of which are referred to herein as medium chain fatty acid derivative compositions, are compositions comprising one or more active components, at least one of the one or more active components has a medium chain fatty acid backbone, and is one that was previously discounted due to a general inability for use internally as an anti-infective and/or as an antimicrobial for a subject in need thereof, the medium chain fatty acid backbone being or originating as dodecanoic acid (lauric acid) and/or having or originating as twelve carbon atoms. Hence, in one or more embodiments, the active component is or includes dodecanoic acid (lauric acid). In some embodiments, includes may constitute comprising. In some embodiments, includes may constitute comprising, in addition to one or more other components, in which said one or more other components do not, on their own, provide bacteriostatic and/or bactericidal activities. In some embodiments, includes may constitute comprising, in addition to one or more active components, in which one or more of said one or more active components on their own may provide some bacteriostatic and/or bactericidal activity. In some embodiments, includes may constitute consisting essentially of, in which the one or more active components consist essentially of lauric acid.

In one or more embodiments, the active component is or includes one or more medium chain fatty acid derivatives, which is based on or originated as a dodecanoic acid (lauric acid). An exemplary medium chain fatty acid backbone being or originating as dodecanoic acid (lauric acid) and/or having or originating as twelve carbon atoms is depicted in FIG. 1, a methyl ester of dodecanoic acid.

The compositions described herein have been prepared in new and useful ways that overcome previous difficulties. The compositions described herein when prepared in any of the new and useful ways, as described herein, may now be so utilized so as to meet at least one of the one or more needs described above. Any one or more of the described compositions may be provided as a direct acting, small molecule agent having fitting antimicrobial properties directed against gram-positive and/or gram-negative pathogens (e.g., harmful and/or infections gram-positive and/or gram-negative organisms) that reside inside or within a subject, in which the direct-acting, small molecule agent comprises one or more active components having or originating with a medium chain fatty acid backbone, or having or originating with 12 carbon atoms. Any one or more of the described compositions may be utilized as a direct-acting, small molecule agent to inhibit activity of one or more gram-positive and/or gram-negative organisms (bacteriostatic activity), and/or for killing one or more certain organisms. Each composition, when prepared in one of the new and useful ways described herein, may include more than one of the described active components (e.g., more than one type). Each composition, when prepared in one of the new and useful ways described herein (with or without more than one of the described active components) may be provided independently, individually, as a direct acting, small molecule agent. A composition, when prepared in one of the new and useful ways described herein (with or without more than one of the described active components) may be provided independently, and in combination with another composition described herein, each composition functioning as a direct acting, small molecule agent. A composition, when prepared in one of the new and useful ways described herein (with or without more than one of the described active components) may be provided in combination with another composition described herein, each composition functioning as a direct acting, small molecule agent. Other agents may also be provided, said other agents acting prophylactically, and/or as an anti-infective, and/or to alleviate one or more symptoms of a subject in receipt of the one or more compositions described herein.

In one or more embodiments, any one or more of the described compositions provided as a direct-acting, small molecule agent, may be utilized to inhibit activity of one or more antibiotic-resistant pathogens, including one or more of the antibiotic-resistant pathogens identified by the WHO Global Priority List.

In one or more embodiments, any one or more of the compositions, including the one or more direct-acting, small molecule agent described herein, include at least one or more medium chain fatty acid as described herein and/or one or more medium chain fatty acid derivative as described herein. In one or more embodiments, a composition described herein includes more than one medium chain fatty acid as described herein and/or more than one medium chain fatty acid derivative as described herein.

In one or more embodiments, a composition as described herein, which includes at least one or more active components, including one or more medium chain fatty acid as described herein and/or one or more medium chain fatty acid derivatives as described herein, is a composition that behaves as a membrane intercalating composition (e.g., intercalating in a membrane of a cell, such as an outer membrane of a target pathogen).

In one or more embodiments, a composition as described herein, which includes at least one or more active components, including one or more medium chain fatty acid as described herein and/or one or more medium chain fatty acid derivative as described herein, is a composition that decreases membrane fluidity and/or normal or usual or previous membrane function (e.g., in a membrane of a cell, such as an outer membrane of a target pathogen).

In one or more embodiments, a composition as described herein, which includes at least one or more active components, including one or more medium chain fatty acid as described herein and/or one or more medium chain fatty acid derivative as described herein, is a composition that causes saturation of a membrane (e.g., a membrane of a cell, such as an outer membrane of a target pathogen).

In one or more embodiments, a composition as described herein, which includes at least one or more active components, including one or more medium chain fatty acid as described herein and/or one or more medium chain fatty acid derivative as described herein, is a composition that inhibits growth of a target, such as a target pathogen.

In one or more embodiments, a composition as described herein, which includes at least one or more active components, including one or more medium chain fatty acid as described herein and/or one or more medium chain fatty acid derivative as described herein, is a composition that inhibits growth of a target in a biologic system, such as a target pathogen in a biologic system.

In one or more embodiments, a composition as described herein, which includes at least one or more active components, including one or more medium chain fatty acid as described herein and/or one or more medium chain fatty acid derivative as described herein, is a composition that kills a target, such as a target pathogen.

In one or more embodiments, a composition as described herein, which includes at least one or more active components, including one or more medium chain fatty acid as described herein and/or one or more medium chain fatty acid derivative as described herein, is a composition that is internalized and kills an internal target, such as an internal target pathogen.

In one or more embodiments, a composition as described herein, which includes at least one or more active components, including one or more medium chain fatty acid as described herein and/or one or more medium chain fatty acid derivative as described herein, is a composition that has better specificity for one or more Gram-positive pathogens as compared with the medium chain fatty acid from which the derivative (as described herein) was derived from. In one or more embodiments, a composition as described herein, which includes at least one or more active components, including one or more medium chain fatty acid as described herein and/or one or more medium chain fatty acid derivative as described herein, is a composition that has better specificity for one or more Gram-positive pathogens as compared with the medium chain fatty acid when used alone, or the medium chain fatty acid derivative when used alone. In one or more embodiments, the Gram-positive pathogen includes an antibiotic resistant pathogen. In one or more embodiments, the Gram-positive pathogen includes an antibiotic resistant pathogen identified by the WHO Global Priority List.

In one or more embodiments, a composition as described herein, which includes at least one or more active components, including one or more medium chain fatty acid as described herein and/or one or more medium chain fatty acid derivatives as described herein, is a composition that has better specificity for one or more Gram-negative pathogens as compared with the medium chain fatty acid from which the derivative (as described herein) was derived from. In one or more embodiments, a composition as described herein, which includes at least one or more active components, including one or more medium chain fatty acid as described herein and/or one or more medium chain fatty acid derivative as described herein, is a composition that has better specificity for one or more Gram-negative pathogens as compared with the medium chain fatty acid when used alone, or the medium chain fatty acid derivative when used alone. In one or more embodiments, the Gram-negative pathogen includes an antibiotic resistant pathogen. In one or more embodiments, the Gram-negative pathogen includes an antibiotic resistant pathogen identified by the WHO Global Priority List.

In one or more embodiments, a composition as described herein, which includes at least one or more active components, including one or more medium chain fatty acid as described herein and/or one or more medium chain fatty acid derivatives as described herein, is a composition that has an improved specificity and a broader target pathogen spectrum for the group selected from one or both Gram-negative pathogens and Gram-negative pathogens, the specificity being better and the target pathogen spectrum being broader than found with the medium chain fatty acid from which the derivative (as described herein) was derived from. In one or more embodiments, the one or both Gram-negative pathogens and Gram-negative pathogens include antibiotic resistant pathogens. In one or more embodiments, the one or both Gram negative pathogens and Gram-negative pathogens includes more than one antibiotic resistant pathogen identified by the WHO Global Priority List.

In one or more embodiments, a medium chain fatty acid derivative composition is described herein, the composition including one or more active components, the one or more active components being or including at least 12-aminododecanoic acid, an example of which is depicted in FIG. 2. In some embodiments, this may also be found as 12-aminododecanoic acid hydrochloride (HCl), and/or a salt thereof. Similarly, an analog thereof, as well as one or more structural and/or functional alternatives, and/or one or more structural and/or functional equivalents may be utilized (not shown). A combination of said one or more 12-aminododecanoic acid, salt, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active components consists essentially of 12-aminododecanoic acid. In some embodiments, including may constitute consisting essentially of, in which the one or more active components consists essentially of any one or more of the one or more 12-aminododecanoic acid, HCl, salt, analog, structural and/or functional alternative, and/or structural and/or functional equivalent, or any combination thereof.

In one or more embodiments, a medium chain fatty acid derivative composition is described herein, the composition including one or more active components, the one or more active components being or including at least 12-amino-1-dodecanoic acid methyl ester, an example of which is depicted in FIG. 3. In some embodiments, this may also be found as 12-amino-1-dodecanoic acid methyl ester HCl and/or a salt thereof. In addition, an analog thereof, as well as one or more structural and/or functional alternatives, and/or one or more structural and/or functional equivalents may be utilized (not shown). A combination of said 12-amino-1-dodecanoic acid methyl ester, salt, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active components consists essentially of 12-amino-1-dodecanoic acid methyl ester. In some embodiments, including may constitute consisting essentially of, in which the one or more active components consists essentially of any one or more of the one or more 12-amino-1-dodecanoic acid methyl ester, HCl, salt, analog, structural and/or functional alternative, and/or structural and/or functional equivalent, or any combination thereof.

In one or more embodiments, a medium chain fatty acid derivative composition is described herein, the composition including one or more active components, the one or more active components being or including at least sucrose monolaurate (sucrose laurate). In one or more embodiments, the sucrose monolaurate may also be found as an analog thereof, as well as one or more structural and/or functional alternatives, and/or one or more structural and/or functional equivalents (not shown). A combination of said sucrose monolaurate, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active components consists essentially of sucrose monolaurate. In some embodiments, including may constitute consisting essentially of, in which the one or more active components consists essentially of any one or more of the one or more sucrose monolaurate, analog, structural and/or functional alternative, and/or structural and/or functional equivalent, or any combination thereof.

In one or more embodiments, a medium chain fatty acid derivative composition is described herein, the composition including one or more active components, the one or more active components being or including at least 12-(7-nitrobenzofurazan-4-ylamino) dodecanoic acid. In one or more embodiments, the 12-(7-nitrobenzofurazan-4-ylamino) dodecanoic acid may also be found as an analog thereof, as well as one or more structural and/or functional alternatives, and/or one or more structural and/or functional equivalents (not shown; e.g., an amine-reactive and/or fluorescent analog, such as 2-(7-nitro-2,1,3-benzoxadiazol-4-ylamino) dodecanoic acid). A combination of said 12-(7-nitrobenzofurazan-4-ylamino) dodecanoic acid, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active components consists essentially of 12-(7-nitrobenzofurazan-4-ylamino) dodecanoic acid. In some embodiments, including may constitute consisting essentially of, in which the one or more active components consists essentially of any one or more of the one or more 12-(7-nitrobenzofurazan-4-ylamino) dodecanoic acid, salt, analog, structural and/or functional alternative, and/or structural and/or functional equivalent, or any combination thereof.

In one or more embodiments, a medium chain fatty acid derivative composition is described herein, the composition including one or more active components, the one or more active components being or including at least 4-nitrophenyl dodecanoate. Similarly, an analog thereof, as well as one or more structural and/or functional alternatives, and/or one or more structural and/or functional equivalents may be utilized (not shown). A combination of said one or more 4-nitrophenyl dodecanoate, salt, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active components consists essentially of 4-nitrophenyl dodecanoate. In some embodiments, including may constitute consisting essentially of, in which the one or more active components consists essentially of any one or more of the one or more 4-nitrophenyl dodecanoate, salt, analog, structural and/or functional alternative, and/or structural and/or functional equivalent, or any combination thereof.

In one or more embodiments, a medium chain fatty acid derivative composition is described herein, the composition including one or more active components, the one or more active components being or including at least 1-lauroyl-rac-glycerol. Similarly, an analog thereof, as well as one or more structural and/or functional alternatives, and/or one or more structural and/or functional equivalents may be utilized (not shown). A combination of said one or more 1-lauroyl-rac-glycerol, salt, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active components consists essentially of 1-lauroyl-rac-glycerol. In some embodiments, including may constitute consisting essentially of, in which the one or more active components consists essentially of any one or more of the one or more 1-lauroyl-rac-glycerol, salt, analog, structural and/or functional alternative, and/or structural and/or functional equivalent, or any combination thereof In one or more embodiments, a medium chain fatty acid derivative composition is described herein, the composition including one or more active components, the one or more active components being or including at least 3-oxo-N-(2-oxocyclohexyl) dodecanamide. Similarly, an analog thereof, as well as one or more structural and/or functional alternatives, and/or one or more structural and/or functional equivalents may be utilized (not shown). A combination of said one or more 3-oxo-N-(2-oxocyclohexyl) dodecanamide, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active component consists essentially of 3-oxo-N-(2-oxocyclohexyl) dodecanamide. In some embodiments, including may constitute consisting essentially of, in which the one or more active components consists essentially of any one or more of the one or more 3-oxo-N-(2-oxocyclohexyl) dodecanamide, analog, structural and/or functional alternative, and/or structural and/or functional equivalent, or any combination thereof.

In one or more embodiments, a medium chain fatty acid derivative composition is described herein, the composition including one or more active components, the one or more active components being or including at least butyl laurate (butyl dodecanoate). Similarly, an analog thereof, as well as one or more structural and/or functional alternatives, and/or one or more structural and/or functional equivalents may be utilized (not shown; e.g., isobutyl dodecanoate). A combination of said one or more butyl laurate, salt, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active components consists essentially of butyl laurate. In some embodiments, including may constitute consisting essentially of, in which the one or more active components consists essentially of any one or more of the one or more butyl laurate, salt, analog, structural and/or functional alternative, and/or structural and/or functional equivalent, or any combination thereof.

In one or more embodiments, a medium chain fatty acid derivative composition is described herein, the composition including one or more active components, the one or more active components being or including at least benzyl laurate. Similarly, an analog thereof, salt, as well as one or more structural and/or functional alternatives, and/or one or more structural and/or functional equivalents may be utilized (not shown). A combination of said one or more benzyl laurate, salt, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active components consists essentially of benzyl laurate. In some embodiments, including may constitute consisting essentially of, in which the one or more active components consists essentially of any one or more of the one or more benzyl laurate, salt, analog, structural and/or functional alternative, and/or structural and/or functional equivalent, or any combination thereof.

In one or more embodiments, a medium chain fatty acid derivative composition is described herein, the composition including one or more active components, the one or more active components being or including at least isoamyl laurate. Similarly, an analog thereof, salt, as well as one or more structural and/or functional alternatives, and/or one or more structural and/or functional equivalents may be utilized (not shown). A combination of said one or more isoamyl laurate, salt, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active components consists essentially of isoamyl laurate. In some embodiments, including may constitute consisting essentially of, in which the one or more active components consists essentially of any one or more of the one or more isoamyl laurate, salt, analog, structural and/or functional alternative, and/or structural and/or functional equivalent, or any combination thereof.

In one or more embodiments, a medium chain fatty acid derivative composition is described herein, the composition including one or more active components, the one or more active components being or including at least monolaurin. Similarly, an analog thereof, as well as one or more structural and/or functional alternatives, and/or one or more structural and/or functional equivalents may be utilized (not shown). A combination of said one or more monolaurin, salt, analog, structural and/or functional alternative, and/or structural and/or functional equivalent, in one or more forms, may also be provided as the one or more active components.

In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active component consists essentially of monolaurin. In some embodiments, including may constitute consisting essentially of, in which the one or more active components consists essentially of any one or more of the one or more monolaurin, salt, analog, structural and/or functional alternative, and/or structural and/or functional equivalent, or any combination thereof.

In one or more embodiments, a medium chain fatty acid derivative composition is described herein, the composition including one or more active components, the one or more active components being or including at least isopropyl laurate. Similarly, an analog thereof, as well as one or more structural and/or functional alternatives, and/or one or more structural and/or functional equivalents may be utilized (not shown). A combination of said one or more isopropyl laurate, salt, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active component consists essentially of isopropyl laurate. In some embodiments, including may constitute consisting essentially of, in which the one or more active components consists essentially of any one or more of the one or more isopropyl laurate, salt, analog, structural and/or functional alternative, and/or structural and/or functional equivalent, or any combination thereof.

In one or more embodiments, a medium chain fatty acid derivative composition is described herein, the composition including one or more active components, the one or more active components being or including at least pentyl laurate. Similarly, an analog thereof, as well as one or more structural and/or functional alternatives, and/or one or more structural and/or functional equivalents may be utilized (not shown). A combination of said one or more pentyl laurate, salt, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active component consists essentially of pentyl laurate. In some embodiments, including may constitute consisting essentially of, in which the one or more active components consists essentially of any one or more of the one or more pentyl laurate, salt, analog, structural and/or functional alternative, and/or structural and/or functional equivalent, or any combination thereof.

In one or more embodiments, a medium chain fatty acid derivative composition is described herein, the composition including one or more active components, the one or more active components being or including at least hexyl laurate. Similarly, an analog thereof, as well as one or more structural and/or functional alternatives, and/or one or more structural and/or functional equivalents may be utilized (not shown). A combination of said one or more hexyl laurate, salt, analog, structural and/or functional alternative, and/or structural and/or functional equivalent, in one or more forms, may also be provided as the one or more active components. In some embodiments, including may constitute comprising. In some embodiments, including may constitute comprising, in addition to one or more other components, in which said one or more other components do not, on their own, provide bacteriostatic and/or bactericidal activities. In some embodiments, including may constitute comprising, in addition to one or more active components, in which one or more of said one or more active components on their own may provide some bacteriostatic and/or bactericidal activity. In some embodiments, including may constitute consisting essentially of, in which the one or more active components consists essentially of hexyl laurate. In some embodiments, including may constitute consisting essentially of, in which the one or more active components consists essentially of any one or more of the one or more hexyl laurate, salt, analog, structural and/or functional alternative, and/or structural and/or functional equivalent, or any combination thereof.

In one or more embodiments, a composition that is or includes at least one or more active components as described above, which is or includes one or more medium chain fatty acid as described herein and/or one or more medium chain fatty acid derivatives as described herein, is miscible with water, and in such a miscible state does not demonstrate inhibitory activity against tested Gram-positive bacteria (e.g., *S. aureus*) or tested gram-negative bacteria (e.g., *E. coli*), as demonstrated in a standard broth microdilution test. For example, 12-aminododecanoic acid that is miscible with water does not, in the miscible state, demonstrate inhibitory activity against one or more Gram-positive bacteria (e.g., *S. aureus*) or against one or more Gram-negative bacteria (e.g., *E. coli*), as demonstrated in the standard broth microdilution test. Similarly, 12-amino-1-dodecanoic acid methyl ester that is miscible with water does not, in the miscible state, demonstrate inhibitory activity against tested Gram-positive bacteria (e.g., *S. aureus*) or against tested Gram-negative bacteria (e.g., *E. coli*), when processed and evaluated similarly in the standard broth microdilution assay. In one or more embodiments, a composition including one or more active components, such as, for example, one of 12-aminododecanoic acid or 12-amino-1-dodecanoic acid methyl ester, each miscible with water, generally, as so prepared, does not demonstrate inhibitory activity against Gram-positive bacteria or Gram-negative bacteria.

In one or more embodiments, an active component, which is or includes one or more medium chain fatty acid as described herein and/or one or more medium chain fatty acid derivatives as described herein, is suspended in an organic solvent, such as chloroform, and/or an organic solvent having a tetrahedral molecular geometry. The organic solvent is preferably evaporatable. Such an active component when suspended in an evaporatable organic solvent forms small particles (e.g., nanoparticles), which remain particles after evaporation of said evaporatable organic solvent. In one or more embodiments, when so prepared, the particulated or particle-containing composition does not, after evaporation of said organic solvent, demonstrate inhibitory activity against tested Gram-positive bacteria (e.g., *S. aureus*) or tested Gram-negative bacteria (e.g., *E. coli*), when evaluated in a standard broth microdilution assay. In some embodiments, a composition including one or more active components, such as, for example, one of 12-aminododecanoic acid or 12-amino-1-dodecanoic acid methyl ester, after evaporation of said organic solvent, as so prepared, may demonstrate minimal, but only very weak, inhibitory activity against one or more Gram-positive bacteria. Generally, with such a preparation, there is no observable inhibitory activity against Gram-negative bacteria.

In one or more embodiments, in preparation for a composition described herein, one or more active components, such as a medium chain fatty acid described herein, and/or a medium chain fatty acid derivative described herein, is combined with lecithin (with or without cholesterol), and further combined and/or coated with chitosan, followed by another process step, such as sonicating. In one or more embodiments, the further process step may include filtering. In one or more embodiments, the further process step may include sonicating, and filtering (e.g., filter sterilizing) after sonicating. When so prepared, a composition may be particulated or contain small particles. In one or more embodiments, a particulated or particle-containing composition is a direct-acting small molecule agent. In one or more embodiments, said composition as a direct-acting small molecule agent is in such a form as to be internalized. In one or more embodiments, said composition as a direct-acting small molecule agent is active against one or both Gram-positive bacteria, particularly pathogenic bacteria (e.g., *S. aureus, S. epidermidis, S. pneumoniae, C. difficile, Mycobacterium* spp., Group A *Streptococcus*, Group B *Streptococcus*, including drug resistant strains), and Gram-negative bacteria, particularly pathogenic bacteria (e.g., *E. coli, A. baumannii, P. aeruginosa*, Enterobacteriaceae, *Campylobacter, Shigella* spp., including drug resistant strains) and yeast (e.g., *Candida*).

In one or more embodiments, when so prepared as described above, a composition comprising an active component, such as at least one of 12-amino-1-dodecanoic acid methyl ester, 12-amino-1-dodecanoic acid, sucrose monolaurate, 12-(7-nitrobenzofurazan-4-ylamino) dodecanoic acid, 4-nitrophenyl dodecanoate, 1-lauroyl-rac-glycerol, 3-oxo-N-(2-oxocyclohexyl) dodecanamide, lauric acid, butyl laurate, benzyl laurate, isoamyl laurate, or monolaurin, and in which the mixture comprising the active component, lecithin, and/or chitosan are at a pH of pH 5 to pH 7 or a pH of about pH 5 to pH 7, will exhibit good inhibitory activity and good growth inhibition of one or more Gram-positive bacteria, particularly pathogenic bacteria (e.g., *S. aureus, S. epidermidis, S. pneumoniae, C. difficile, Mycobacterium* spp., Group A *Streptococcus*, Group B *Streptococcus*, including drug resistant strains). The good inhibitory activity and good growth inhibition against Gram-positive bacteria is greater, and generally significantly greater than the extremely weak or negligible activity associated with a composition having the same active component that was instead prepared with simply an evaporatable organic solvent, or when the active component was used alone.

In one or more embodiments, when charge distribution of the particulated or particle-containing compositions are altered, such as when: (a) in preparation, the mixture comprising the active component, lecithin, and/or chitosan are at an alkaline pH (e.g., pH 9); or (b) when, in preparation, such a mixture is at an acidic or neutral pH and includes a certain chemical agent in the mixture that imparts a positive charge to the surface of the particulated or particle-containing composition (such as glycol chitosan), there is a rather unexpected finding, in which one or more of the active components, when so treated, and formed in a particulated or particle-containing composition, exhibit a more broad spectrum activity, showing good antimicrobial activity against both Gram-positive bacteria, particularly pathogenic bacteria, as well as Gram-negative bacteria, particularly pathogenic bacteria. This unexpected phenomenon is generally found with certain preparation conditions, as outlined herein (both above and later below), and with some of the one or more active components, including with at least 12-aminododecanoic acid, 12-amino-1-dodecanoic acid, and sucrose monolaurate, and their suitable analogs considered structural and/or functional alternatives, and/or structural and/or functional equivalents.

In one or more embodiments, a particulated or particle-containing composition, as described herein, which includes at least the one or more active components, including one or more medium chain fatty acid as described herein and/or one or more medium chain fatty acid derivatives as described herein, may be manipulated to improve inhibitory activity against Gram-positive bacteria, including Gram-positive pathogenic bacteria, and drug resistant strains thereof. For this, the particulated composition will include at least one of an active component that has 12 carbon atoms and at least one methyl and/or ethyl side chain.

In one or more embodiments, a particulated or particle-containing composition (which, when used herein, may also be one or more particulated or particle-containing compositions), as described herein, which includes at least the one or more active components, including one or more medium chain fatty acid derivatives as described herein, may be further manipulated to impart inhibitory activity against both Gram-positive (including Gram-positive pathogenic bacteria, and drug resistant strains thereof) as well as Gram-negative bacteria (including Gram-negative pathogenic bacteria, and drug resistant strains thereof. For this broad-spectrum activity, the particulated or particle-containing composition will, unexpectedly, have to include a plurality of characteristics, that were not previously apparent. For example, the one or more active components will need to be positively charged, and will be an active component with a 12-carbon atom backbone that is hydrophobic (generally being more strongly hydrophobic, with a Log P value that is less than 4). When such an active component further comprises at least one methyl and/or ethyl side chain, its overall inhibitory activity, may also increase. A positive charge provided to the particulated composition may be delivered by including, in the preparation for the particulated composition, more than one of the following: (i) a positively charged carrier, (ii) a positively charged chitosan, (iii) one or more active components in which at least one of the active components has a 12-carbon atom backbone, (iv) at least one methyl and/or ethyl side chain on the one or more active components (e.g., on the 12-carbon atom backbone), (v) one or more active components in which at least one of the one or more active components is strongly hydrophobic (e.g., generally, associated with a Log P value that is less than 4). In some embodiments, a positive charge is conferred by at least (ii), (iii), and (v). In some embodiments, a positive charge is conferred by at least (i), (iii), and (v). Examples of suitable and representative active components that meet the criteria of (iii), (iv), and/or (v) are 12-aminododecanoic acid, 12-amino-1-dodecanoic acid methyl ester, and sucrose monolaurate. Hence, in one or more embodiments, more than one composition as described herein, which includes one or more active components described herein, which includes one or more medium chain fatty acid as described herein and/or one or more medium chain fatty acid derivatives as described herein, when used alone or in combination, may be manipulated to confer additional inhibitory activity against one or more Gram-negative bacteria.

In one or more embodiments, more than one composition as described herein, which includes one or more active components, including one or more medium chain fatty acid as described herein and/or one or more medium chain fatty acid derivatives as described herein, and when prepared as described herein (particulated and/or not particulated) to impart inhibitory activity against one or more pathogens, may be utilized and/or harnessed, alone or in combination, as a direct acting, small molecule agent, with a good safety profile. Generally, any of the one or more described compositions, when provided alone or in combination with a similar composition having one or more active components described herein, will cause instability of a targeted pathogen (e.g., membrane instability, such as decreased fluidity, and/or decreased membrane function) and/or will inhibit growth of the targeted pathogen.

The described composition, alone or in combination with a similar composition having a sufficient amount of one or more active components, may be further provided to a subject as an antimicrobial. The sufficient amount of the one or more active components in the antimicrobial may be sufficient for bacteriostatic activity. The sufficient amount of the one or more active components in the antimicrobial may be sufficient for bactericidal activity. The sufficient amount of the one or more active components in the antimicrobial may be for prophylactic use. The sufficient amount of the one or more active components in the antimicrobial may be for treatment against one or more susceptible pathogens. The sufficient amount of the one or more active components in the antimicrobial may be for treatment against one or more susceptible and antibiotic-resistant pathogens, including one or more susceptible and antibiotic-resistant pathogens identified by the WHO Global Priority List. Any of the described compositions as direct-acting, small molecule agents, alone or in combination with a similar composition having one or more active components, and when in use, either with or without another agent (one not containing the composition described herein), may be provided in one or more suitable, safe, and effective formulations, such as for topical use and/or for internal use. When for internal use, the described composition may be formulated for oral ingestion. When for internal use, the described composition may be formulated for injection. When for internal use, the described composition may be formulated for inhalation. When prepared and/or when for use, the one or more described active components and/or described compositions may have GRAS status.

In one or more embodiments, described herein is a composition for bacteriostatic action against at least one of one or more Gram-positive bacteria and/or one or more Gram-negative bacteria, the composition comprising at least one of a medium chain fatty acid, which, in some instances is lauric acid, and/or a medium chain fatty acid derivative, which, in some instances may be referred to as a lauric acid derivative. When such a composition comprises a lauric acid derivative, this may be selected from, but is not limited to, one or more of 12-aminododecanoic acid, 12-amino-1-dodecanoic acid methyl ester, sucrose monolaurate, 12-(7-nitrobenzofurazan-4-ylamino) dodecanoic acid, 4-nitrophenyl dodecanoate, 1-lauroyl-rac-glycerol, 3-oxo-N-(2-oxocyclohexyl) dodecanamide, butyl laurate, benzyl laurate, isoamyl laurate, monolaurin, isopropyl laurate, pentyl laurate, hexyl laurate (or suitable analog, generally a structural and/or functional alternative, and/or structural and/or functional equivalent). In some embodiments, a composition is for bacteriostatic action against at least one Gram-positive bacteria, and at least one Gram-negative bacteria, the composition comprising a medium chain fatty acid derivative, sometimes referred to as a lauric acid derivative. Such a lauric acid derivative may be selected from at least one of 12-aminododecanoic acid, 12-amino-1-dodecanoic acid methyl ester, and sucrose monolaurate, as representative examples. Such a lauric acid derivative may be selected from one that, when prepared, imparts a positive charge to the particulated or particle-containing composition, and, as an active component, includes the following characteristics: (a) has a 12-carbon atom backbone; and (b) is strongly hydrophobic (e.g., has a Log P value that is less than 4). In addition, or as an alternative, such a lauric acid derivative may have the following characteristics: (a) a 12-carbon atom backbone and at least one methyl and/or ethyl side chain on the 12-carbon atom backbone, and (b) is strongly hydrophobic (e.g., has a Log P value that is less than 4).

Any of the described compositions, or direct-acting, small molecule agents, may further comprise lecithin. Any of the described compositions, or direct-acting, small molecule agents, may further comprise lecithin and cholesterol. Any of the described compositions, or direct-acting, small molecule agents, may further comprise lecithin (with or without cholesterol) and a carrier. Any of the described compositions, or direct-acting, small molecule agents, may further comprise lecithin (with or without cholesterol) and chitosan. In one or more embodiments, the carrier and/or chitosan may be positively charged (or formulated so by preparing in an alkaline pH, or by imparting positivity via addition of at least one certain chemical agent, such as described herein).

Any of the described compositions, or direct-acting, small molecule agents, may further comprise one or more bacteria, such as one or more bacterial species described herein.

Any of the described compositions, or direct-acting, small molecule agents, when provided as described herein, may include particulates or may be particulated. The particulates may be or may include nanoparticles.

Any of the described compositions, or direct-acting, small molecule agents, when provided in a form as described herein, may be or are suitable for use or are for utilization in a formulation for oral delivery.

Any of the described compositions, or direct-acting, small molecule agents, when provided in a form as described herein, may be or are suitable for use or are for utilization in a formulation for topical delivery.

Any of the described compositions, or direct-acting, small molecule agents, when provided in a form as described herein, may be or are suitable for use or are for utilization in a formulation for injection or for injectable delivery.

Any of the described compositions, or direct-acting, small molecule agents, when provided in a form as described herein, may be or are suitable for use or are for utilization in a formulation for inhalation or for inhaled delivery.

Any of the described compositions, or direct-acting, small molecule agents, when provided in a form as described herein, may be or are suitable for use or are for utilization in a formulation for intramuscular delivery.

Any of the described compositions, or direct-acting, small molecule agents, when provided in a form as described herein, may be or are suitable for use or are for utilization in a formulation for intravenous delivery.

In a composition as described herein, the lauric acid or the one or more lauric acid derivatives is in an amount between about 0.001 wt. % and about 30 wt. % of the composition, or may be in any suitable range or sufficient range therebetween. In a composition as described herein, the lecithin is in an amount up to about 10 wt. % of the composition, or may be in any suitable amount or range of amounts therein. In a composition as described herein, the lecithin may be or is in an amount up to about 30 wt. % of the composition, or may be in any suitable amount or range of amounts therein. In a composition as described herein, the chitosan (positively charged or not) may be or is in an amount up to about 10 wt. % of the composition, or may be in any suitable amount or range of amounts therein. The chitosan, in a composition as described herein, may be or is in an amount up to about 30 wt. % of the composition, or may be in any suitable amount or range of amounts therein.

The composition may be or may comprise particulates. The composition may be or is sonicated to form particulates. The composition (particulated or not) may be or is a suspension. The composition (particulated or not) may be or is filtered. The composition may be or is a dry or powder form. The composition may be or is sterilized. The composition may further comprise an excipient, generally an excipient that is at least pharmaceutically acceptable, and may be an excipient that is at least pharmaceutically acceptable for internal delivery of the composition. The excipient may comprise a sufficient amount of one or more pharmaceutically acceptable excipients for suitable delivery of the composition.

The compositions described herein may, and generally do, when utilized on or against one or more susceptible pathogen types or one or more susceptible pathogen strains, inhibit growth of the one or more susceptible pathogen types or the one or more susceptible pathogen strains. The one or more susceptible pathogen types or the one or more susceptible pathogen strains generally include at least one or more susceptible Gram-positive bacterial strains. The Gram-positive bacterial strain may be a pathogenic bacteria, including *S. aureus, S. epidermidis, S. pneumoniae, C. difficile, Mycobacterium* spp., Group A *Streptococcus*, and Group B *Streptococcus*. The Gram-positive bacterial strain may be a pathogenic bacteria that is drug resistant (e.g., methicillin-resistant *Staphylococcus aureus*, vancomycin resistant *Staphylococcus aureus*). The one or more susceptible pathogen types or the one or more susceptible pathogen strains may also include at least one or more susceptible Gram-negative bacterial strains. The Gram-negative bacterial strain may be a pathogenic bacteria, including Enterobacteriaceae, *E. coli, A. baumannii, P. aeruginosa*, Enterobacteriaceae, *Campylobacter, and Shigella* spp. The Gram-negative bacterial strain may be a pathogenic bacteria that is drug resistant (e.g., carbapenem-resistant *Acinetobacter baumannii*, carbapenem-resistant *Pseudomonas aeruginosa*, carbapenem-resistant Enterobacteriaceae, cephalosporin-resistant Enterobacteriaceae, fluoroquinolone-resistant *Campylobacter*, fluoroquinolone-resistant *Salmonella* spp., fluoroquinolone-resistant *Shigella* spp.). The one or more susceptible pathogen types or the one or more susceptible pathogen strains may also include yeast (e.g., *Candida*). The composition may be provided for exposure to (or with) the one or more susceptible pathogen types or the one or more susceptible pathogen strains. When provided, the composition may be provided serially. When provided, the composition may be provided at an inhibitory concentration (inhibitory with respect to at least one of the one or more susceptible pathogen types and/or the one or more susceptible pathogen strains). When provided, the composition may be provided below an inhibitory concentration (sub-inhibitory with respect to the one or more susceptible pathogen types and/or the one or more susceptible pathogen strains). When provided, the composition may be provided for bacteriostatic activity. When provided, the composition may be provided for bactericidal activity.

In one or more embodiments is a method of making a composition described herein, such a composition will have bacteriostatic action against one or more susceptible pathogen types or the one or more susceptible pathogen strains. Such a composition may have bactericidal activity against the one or more susceptible pathogen types or the one or more susceptible pathogen strains. The one or more susceptible pathogen types or the one or more susceptible pathogen strains generally include at least one or more susceptible Gram-positive bacterial strains, including *S. aureus, S. epidermidis, S. pneumoniae, C. difficile, Mycobacterium* spp., Group A *Streptococcus*, and Group B *Streptococcus*. The one or more susceptible pathogen types or the one or more susceptible pathogen strains may include one or more susceptible Gram-positive bacterial strains and/or one or more susceptible Gram-negative bacterial strains, in which the one or more susceptible Gram-negative bacterial strains include Enterobacteriaceae, *E. coli, A. baumannii, P. aeruginosa*, Enterobacteriaceae, *Campylobacter*, and *Shigella* spp. The method may comprise suspending with an organic solvent, such as a low VOC solvent, at least one of the one or more medium chain fatty acid (lauric acid) and/or at least one of the one or more medium chain fatty acid derivatives as described herein, to form a suspension. The lauric acid derivative is selected from at least one of 12-aminododecanoic acid, 12-amino-1-dodecanoic acid methyl ester, sucrose monolaurate, 12-(7-nitrobenzofurazan-4-ylamino) dodecanoic acid, 4-nitrophenyl dodecanoate, 1-lauroyl-rac-glycerol, 3-oxo-N-(2-oxocyclohexyl) dodecanamide, butyl laurate, benzyl laurate, isoamyl laurate, monolaurin, isopropyl laurate, pentyl laurate, and hexyl laurate (or suitable analog, generally a structural and/or functional alternative, and/or structural and/or functional equivalent). The solvent may be chloroform. The method may further comprises mixing the suspension with water. The method may further comprise combining the suspension with a lecithin. The lecithin may be in a solution or mixture. The lecithin solution or mixture may be an acidic solution or mixture. The lecithin solution or mixture may be a neutral solution or mixture. The lecithin solution or mixture may be an alkaline solution or mixture. The method may further comprise including cholesterol to the suspension with the lecithin. In some embodiments, the method may further comprise combining the suspension with the lecithin (and with or without the cholesterol) with a carrier or chitosan. The carrier or chitosan may be in a solution or mixture. The carrier or chitosan solution or mixture may be an acidic solution or mixture. The carrier or chitosan solution or mixture may be a neutral solution or mixture. The carrier or chitosan solution or mixture may be an alkaline solution or mixture. In some embodiments, the carrier or chitosan solution or mixture may be the same as the lecithin solution or mixture. The carrier or the chitosan may be positively charged. In addition, or as an alternative, a chemical agent imparting a positive charge to the carrier or chitosan may be included. The method further comprises or may further comprise sonicating the suspension in the solution or mixture with the lecithin (with or without the cholesterol, with or without the carrier or chitosan, with or without the chemical agent imparting the positive charge to the carrier or chitosan). The method further comprises or may further comprise filtering after sonicating. The method may comprise filtering without sonicating. With sonicating (and with or without filtering), the method provides a composition having or comprising small particles. The small particles may be or may include nanoparticles. With any of the described methods, a composition prepared by any of the described compositions may be provided in a formulation, and may be suitable for use as the formulation. The formulation may comprise one or more excipients, fillers, and the like, as is known in the art, in which the one or more excipients, fillers, and the like, are each in a sufficient amount, in a form that is pharmaceutically acceptable, and appropriate for the manner of delivery.

The composition described herein or the formulation described herein may be prepared in a manner described herein, and suitable for topical delivery. The composition described herein or the formulation described herein may be prepared in a manner described herein, and suitable for internal use, such as for a subject in need thereof. The composition described herein or the formulation described herein may be prepared in a manner described herein, and suitable for oral delivery. The composition described herein or the formulation described herein may be prepared in a manner described herein, and suitable for inhaled delivery. The composition described herein or the formulation described herein may be prepared in a manner described herein, and suitable for intravenous delivery. The composition described herein or the formulation described herein may be prepared in a manner described herein, and suitable for intramuscular delivery. The composition or the formulation so prepared as described herein will inhibit growth of the one or more susceptible pathogen type or the one or more susceptible pathogen strains described herein. The composition or the formulation so prepared as described herein may be provided for exposure to (or with) the one or more susceptible pathogen type or the one or more susceptible pathogen strain described herein.

When provided in any of the forms described herein, the composition or the formulation so prepared as described herein, may be provided serially. When provided in any of the forms described herein, the composition or the formulation so prepared as described herein, may be provided at an inhibitory concentration (inhibitory with respect to at least one, or more than one, of the one or more susceptible pathogen types and/or the one or more susceptible pathogen strains described herein). When provided in any of the forms described herein, the composition or the formulation so prepared as described herein, may be provided below an inhibitory concentration (sub-inhibitory with respect to at least one, or more than one, of the one or more susceptible pathogen types and/or the one or more susceptible pathogen strains described herein).

With any of the methods described herein, the composition or the formulation described herein that is prepared as described herein, may include or may provide, in at least one form, a direct acting, small molecule agent that displays bacteriostatic and/or bactericidal activity against one or more susceptible pathogen types or one or more susceptible pathogen strains. With any of the methods described herein, the composition or the formulation described herein that is prepared as described herein, may include or may provide, in at least one form, a direct acting, small molecule agent that displays inhibitory activity against one or more susceptible pathogens, including one or more drug-resistant pathogens.

These and other embodiments are described herein.

BRIEF DESCRIPTION OF THE DRAWINGS

For a more complete understanding of the description provided herein and the advantages thereof, reference is now made to the brief description of the drawings below, taken in connection with the accompanying drawings and with the description.

DESCRIPTION OF REPRESENTATIVE EMBODIMENTS

Figure 1:
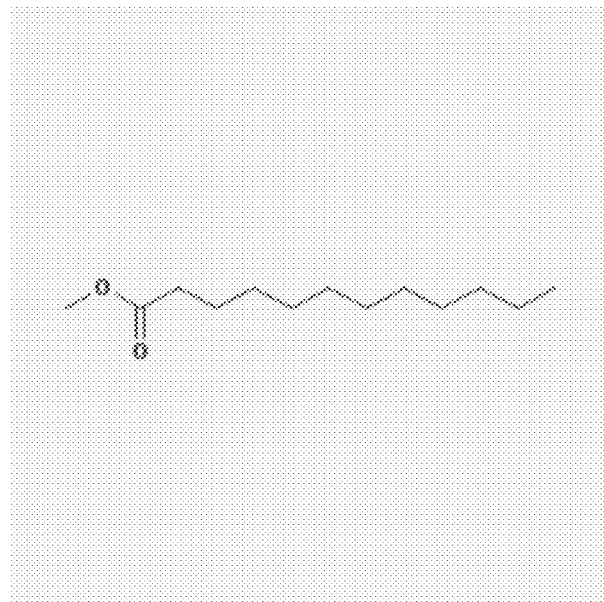
FIG. 1 depicts a representative structure of a medium chain fatty acid, lauric acid, with a methyl ester.
Figure 2:
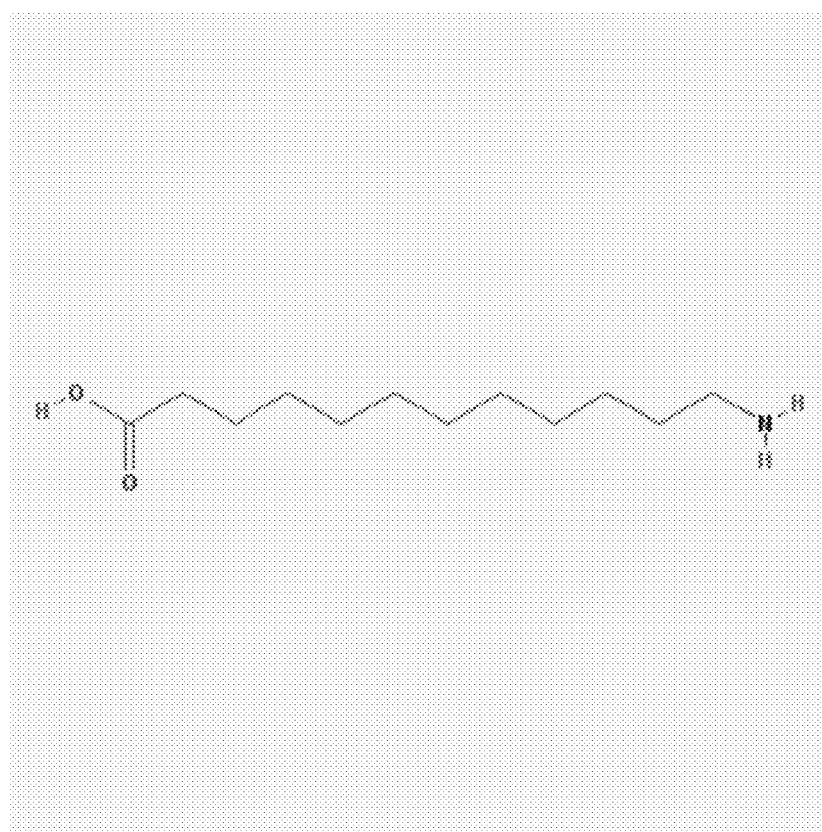
FIG. 2 depicts a representative structure of 12-aminododecanoic acid, as described herein.
Figure 3:
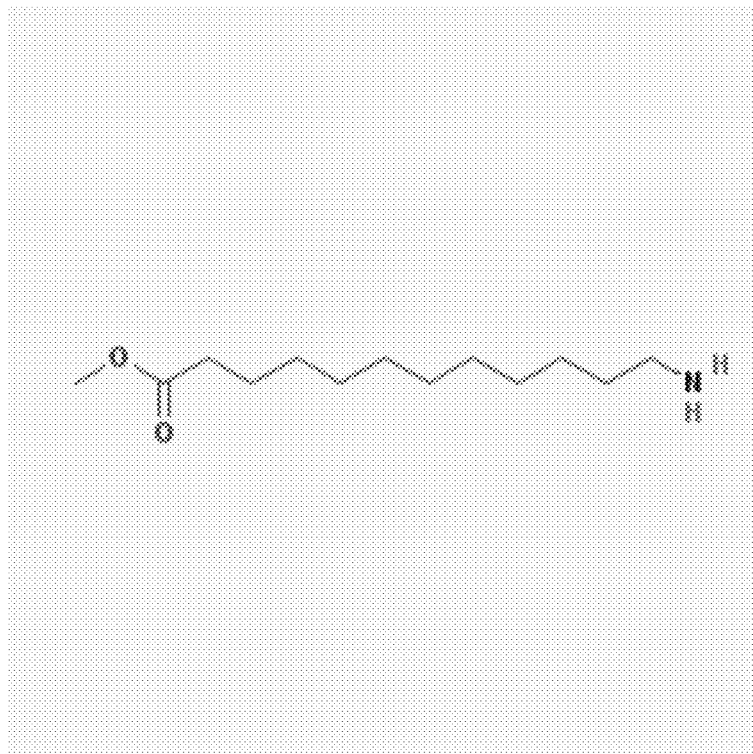
FIG. 3 depicts a representative structure of 12 amino-1-dodecanoic acid methyl ester, as described herein.
Figure 4:
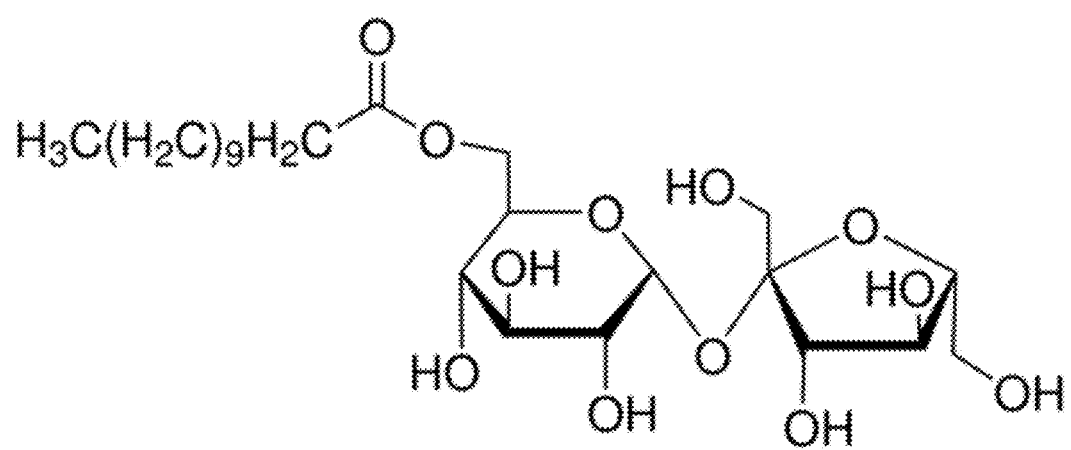
FIG. 4 depicts a representative structure of sucrose monolaurate, as described herein.

Although making and using various embodiments are discussed in detail below, it should be appreciated that as described herein are provided many inventive concepts that may be embodied in contexts outlined and/or contemplated herein and/or interpreted or varied by the skilled artisan. Embodiments discussed herein are merely representative and do not limit the scope of the invention.

Compositions described herein comprise one or more active components, the active component may comprise one or more of a specific derivative and/or synthetic by-product of a medium chain fatty acid, lauric acid, or may be or include a medium chain fatty acid, lauric acid. When prepared in the manner described herein, the lauric acid, or the derivatives and/or synthetic by-products of the medium chain fatty acid, lauric acid, may be utilized internally in a safe and effective manner for effective bacteriostatic action and/or bactericidal action against one or more susceptible pathogens, and in which the more susceptible pathogens include internal susceptible pathogens. In one or more embodiments, each specific and/or representative derivative and/or synthetic by-product of lauric acid, including those embodied herein and/or as described herein, are provided in a composition, as described or as embodied herein. The compositions described herein have unexpected outcomes, and have been prepared to allow the lauric acid or lauric acid derivative to be provided internally and in a manner that allows, with internal utilization, internal bacteriostatic and/or bactericidal activity against susceptible pathogens. In one or more embodiments, when the lauric acid, or the derivatives and/or synthetic by-products of the medium chain fatty acid, lauric acid, are so provided in a composition described herein, the composition was found unexpectedly to preserve activity of the active component, and, thereby, allowing the composition containing the active component to exhibit improved action or improved function, especially in prevention of growth, which has not been found by others. In addition or as an alternative, in one or more embodiments, when the lauric acid, or the derivatives and/or synthetic by-products of the medium chain fatty acid, lauric acid, are so provided in a composition described herein, the composition was prepared in a manner that unexpectedly preserved activity of the active component, and, thereby, allowed the composition containing the active component to exhibit improved action or improved function, especially in prevention of growth of a susceptible pathogen, which has not been found by others. Such improved action or improved functions described herein show that the one or more active components described herein will, when provided internally, be effective as a bacteriostatic agent, preventing growth of a susceptible pathogen, and providing bacteriostatic activity better than a same active component that is used alone without being prepared in a composition as described herein. Such improved action or improved functions described herein show that the one or more active components described herein will, when provided internally, be effective as a bactericidal agent, killing at least some of the susceptible pathogen, and providing bactericidal activity better than a same active component used alone without being prepared in a composition as described herein. For example, each specific derivative and/or synthetic by-product of lauric acid, as described and/or as embodied herein, may be provided in a composition, in a manner as described herein, and when so provided in such a composition, has bacteriostatic activity against one or more susceptible target pathogens, which includes one or more internal susceptible target pathogens, and inhibiting as well as preventing growth of the one or more susceptible target pathogens. In some instances, with such a composition, as described and/or as embodied herein, there is activity, where no activity was found before. In some instances, with such a composition, as described and/or as embodied herein, there is significantly better activity, where only weak activity was found before. In some embodiments, the one or more susceptible target pathogens include at least one or more than one susceptible Gram-positive bacterial strain. In some embodiments, the one or more susceptible target pathogens are at least one, or more than one, susceptible antibiotic resistant Gram-positive bacterial strain. In some embodiments, the one or more susceptible target pathogens include at least one, or more than one, susceptible Gram-positive bacterial strain as well as at least one, or more than one, susceptible Gram-negative bacterial strain. In one or more embodiments, some of the specific derivatives and/or synthetic by-products of lauric acid as described and/or as embodied herein were found, unexpectedly, to be capable of a certain and unique manner of manipulation to directly influence function and activity of a final composition. In some embodiments, the manner of manipulation could increase the inhibitory effect or bacteriostatic activity of the so-manipulated composition against the at least one or more than one susceptible Gram-positive bacterial strains. In some embodiments, the manner of manipulation could directly influence inhibitory or bacteriostatic activity of the so-manipulated composition and the type of pathogen that is susceptible to the so-manipulated composition, such that more than one type of pathogen becomes susceptible to the so-manipulated composition. These and other considerations are further described below.

In one or more embodiments, the one or more active components, including one or more medium chain fatty acid as described herein and/or one or more medium chain fatty acid derivatives, as described herein, is miscible with water. In one or more embodiments, the one or more active component, including one or more medium chain fatty acid as described herein and/or one or more medium chain fatty acid derivatives as described herein, is suspended in an organic solvent, such as chloroform, and/or an organic solvent having a tetrahedral molecular geometry. Generally, with such preparations, and when evaluated further in vitro, such as in a microdilution assay against a Gram-positive or a Gram-negative pathogen, the one or more active components were not effective at inhibiting growth of the Gram-positive pathogen or the Gram-negative pathogen. As such, the one or more active components were found, unexpectedly, to require a number of more complicated steps in order to exhibit selective bacteriostatic activity (and/or bactericidal activity), and to require certain characteristics and even further manipulation in order to exhibit a broad-spectrum activity (e.g., inhibitory and/or killing activity against at least certain Gram-positive bacteria as well as Gram-negative bacterial strains), and/or calculatable and significant improvements in its selective activity (e.g., against Gram-positive bacterial strains). In one or more embodiments, the manner of manipulation described herein is contrary to previous findings described by others.

In a first embodiment is described at least an active lauric acid derivative, 12-aminododecanoic acid. In another embodiment is described at least an active lauric acid derivative, 12-amino-1-dodecanoic acid methyl ester. In still another embodiment is a combination of at least the active lauric acid derivatives, 12-aminododecanoic acid and 12-amino-1-dodecanoic acid methyl ester. In yet another embodiment is at least an active lauric acid derivative, sucrose monolaurate. In still another embodiment is a combination of at least two or more of the active lauric acid derivatives selected from 12-aminododecanoic acid, 12-amino-1-dodecanoic acid methyl ester, and sucrose monolaurate. In still another embodiment is a combination of at least two or more of the active lauric acid derivatives that include 12-aminododecanoic acid, 12-amino-1-dodecanoic acid methyl ester, and sucrose monolaurate. In yet another embodiment is at least one or more of an active lauric acid derivative, in which the active lauric acid derivative is selected from one having the following characteristics: (a) a 12-carbon atom (C12) backbone; and (b) considered hydrophobic, e.g., having a Log P value that is less than 4. In addition, or as an alternative, the at least one or more of the lauric acid derivative of any of the above embodiments may have the following characteristics: (a) a 12-carbon atom backbone and at least one methyl and/or ethyl side chain on the 12-carbon atom backbone, and (b) considered strongly hydrophobic, e.g., having a Log P value that is less than 4. With each of said above-identified embodiments, when the one or more active lauric acid derivative is prepared in at least one composition as described herein, the at least one composition, when tested with susceptible pathogens, was found to exhibit broad spectrum antimicrobial activity, demonstrating inhibitory activity (growth inhibition) against one or more Gram-positive bacterial strains (e.g., the one or more including one or more of *S. aureus, S. epidermidis, S. pneumoniae, C. difficile, Mycobacterium* spp., Group A *Streptococcus*, Group B *Streptococcus*, including drug resistant strains), as well as inhibitory activity (growth inhibition) against Gram-negative bacteria (e.g., the one or more including one or more of Enterobacteriaceae, *E. coli, A. baumannii, P. aeruginosa,* Enterobacteriaceae, *Campylobacter, Shigella* spp., including drug resistant strains) and yeast (e.g., *Candida*). The broad-spectrum activity was unexpected. The broad-spectrum activity was unexpected and was not found when any one of the above identified active components (consisting of the lauric acid derivative described above) was used alone and, hence, was not prepared in a composition as further described herein (data not shown). The minimal inhibitory concentration (MIC) and broad-spectrum activity was sufficient to utilize the at least one composition in a formulation for internal delivery of the composition. And, with any such composition preparation, and for any such compositions prepared therefrom, a formulation for internal delivery with suitable or sufficient inhibitory activity (growth inhibition) against many, or most, or all Gram-negative bacterial strains will be found.

In a manner of preparation of the one or more compositions described above, and in a condition in which such a composition is prepared, in which a preparatory mixture comprises at least lecithin (or one or more variants thereof, with or without cholesterol), and a carrier or chitosan, as well as a suitable active component (or one or more suitable active components as described above), the composition is prepared in a mixture that is at an alkaline pH (e.g., about pH 9, as an example). This is contrary to previous findings, in which others have found fatty acids to provide their best activity in an acidic environment. It is further noted that the composition described herein have not been previously described. In addition, the compositions as described above then demonstrated the broad-spectrum activity, with inhibitory activity (preventing growth) against susceptible Gram-positive bacterial strains and susceptible Gram-negative bacterial strains. (See also TABLE 2, in which maximum concentration of each composition tested was 10 mg/ml, and in which testings also included a positive control for inhibitory activity against the tested Gram-positive bacterial strain, which included octanoic acid, having 8 carbon atoms, and decanoic acid, having 10 carbon atoms). Said compositions described herein, when compared to its fatty acid alone (e.g., absent the preparation described herein) exhibited significantly better in vitro growth inhibitory activity (not all data shown).

In an alternative manner of preparation of one or more compositions utilizing one or more active components described above, and to illicit broad spectrum activity, a preparatory mixture may comprise at least lecithin (or one or more variants, thereof, with or without cholesterol), a carrier or chitosan, as well as a suitable active component (or one or more suitable active components as described above), and is not alkaline, and is, instead, at least at a neutral pH (e.g., about pH 7), and in which the preparatory mixture used to prepare such a composition further comprises a certain chemical agent that imparts a positive charge to the carrier or the chitosan in the preparatory mixture. (See, again, TABLE 2). Said compositions, when compared in vitro to its fatty acid alone (e.g., absent the preparation described herein) exhibited significantly better in vitro growth inhibitory activity (not all data shown). An example of such a chemical agent that may be utilized in the alternative manner of preparation is glycol. Additional representative chemical agents that may be utilized include but are not limited to polyethylene glycol, acrylate, and a chemical prepared in a quaternization process with a quaternary compound (e.g., a cation consisting having a central positively charged atom with four substituents that are generally, or especially organic groups, such as alkyl and aryl groups, including but not limited to quaternary ammonium salts). These and other chemical agents suitable of imparting a strong positive charge are contemplated herein.

Without being bound by theory, the above and unexpected findings suggest a hydroxyl dominant environment for synthesis of a composition of the embodiments and active components described above, in order to achieve, when internalized, sufficient inhibitory activity against the susceptible pathogens and/or the improvements in inhibitory activity against the susceptible pathogens. This hydroxyl dominant environment is in the preparatory mixture containing the carrier or chitosan, which allowed such a composition, when so prepared, to become more active (e.g., exhibiting strong inhibitory activity) against not only susceptible Gram-positive bacterial strains, but also against susceptible Gram-negative bacterial strains. Without being bound by theory, the hydroxyl dominant environment is believed to promote formation of positively charged carrier or chitosan, which when included in a formed composition containing or comprising particles, will provide positively charged particles. The hydroxyl dominant environment that promotes formation of positively charge particles will occur at an alkaline pH, such as pH 9. Similarly, positively charged particles are created with an innately charged chitosan, in which a certain chemical agent (e.g., glycol) carries an innate positive charge at a neutral pH (pH 7).

With still further analysis, as is described briefly below, in addition to the hydroxyl dominant environment of said composition, there is, on one or more embodiments, an additional requirement for synthesis of one or more compositions of the embodiment described above, which includes having a suitable active component (or one or more suitable active components) as described above. Having an active component with a 12-carbon atom backbone appears necessary for a composition of the embodiment described above to exhibit inhibitory activity against a Gram-negative pathogen. (See, e.g., TABLE 2).

TABLE 1

| Active lauric acid derivative | MIC (mg/ml) for S. epidermidis (chitosan prep. mixture was at pH 5 or at pH 7) | MIC (mg/ml) for E. coli (chitosan prep. mixture was at pH 5 or at pH 7) |
| --- | --- | --- |
| 12-aminododecanoic acid | 10 | — (no inhibitory activity) |
| 12-amino-1-dodecanoic acid methyl ester HCl | 10 | — (no inhibitory activity) |
| sucrose monolaurate | 10 | — (no inhibitory activity) |
| octanoic acid | 10 | — (no inhibitory activity) |
| decanoic acid | 10 | — (no inhibitory activity) |

TABLE 2

| Active lauric acid derivative | MIC (mg/ml) for E. coli (chitosan prep. mixture was at pH 9) | MIC (mg/ml) for E. coli (chitosan prep. mixture was at pH 7 with glycol chitosan) |
| --- | --- | --- |
| 12-aminododecanoic acid | 10 | 10 |
| 12-amino-1-dodecanoic acid methyl ester HCl | 10 | 0.8 |
| sucrose monolaurate | 10 | 10 |
| octanoic acid | — (no inhibitory activity) | — (no inhibitory activity) |
| decanoic acid | — (no inhibitory activity) | — (no inhibitory activity) |

In still further embodiments, also referred to herein as second embodiment (which does not mean nor imply that there are only two embodiments, as is clear from the full description provided herein), are still further, or additional, active components selected from lauric acid, as well as representative active lauric acid derivatives, which include, but are not limited to, at least, 12-(7-nitrobenzofurazan-4-ylamino) dodecanoic acid, 4-nitrophenyl dodecanoate, 1-lauroyl-rac-glycerol, 3-oxo-N-(2-oxocyclohexyl) dodecanamide, butyl laurate, benzyl laurate, isoamyl laurate, monolaurin, isopropyl laurate, pentyl laurate, hexyl laurate, as well as any combination of lauric acid and/or such additional active lauric acid derivatives (as well as a suitable analog or salt form, represented as a structural and/or functional alternative, and/or structural and/or functional equivalent, or any combination thereof). Compositions prepared with one or more of these additional active components of the second embodiment, and when tested in vitro, were found to exhibit selective activity, with good inhibitory (growth inhibition) activity against only susceptible Gram-positive pathogens, the susceptible Gram-positive pathogens including one or more of S. aureus, S. epidermidis, S. pneumoniae, C. difficile, Mycobacterium spp., Group A Streptococcus, and Group B Streptococcus (including drug resistant strains). Moreover, as exemplified in TABLES 1, 2, 3, compositions prepared with one or more of these additional active components of the second embodiment, and when tested in vitro, exhibited, in general, no inhibitory activity against a representative Gram-negative bacterial pathogen. (See TABLES 1, 2, 3, in which maximum concentration of each composition tested was 10 mg/ml against the tested representative Gram-positive bacteria, and in which testings also included positive controls, octanoic acid, having 8 carbon atoms, and decanoic acid, having 10 carbon atoms; prep.=preparation). Such findings were unexpected, and not found when any one of the additional active components was used alone and, hence, when not prepared in a composition as described (data not shown). The minimal inhibitory concentration (MIC) and selective activity was sufficient to utilize any one or more of the additional active components, when prepared in a composition and provided in a formulation, for internal delivery of the composition. This does not mean that combinations of active components (e.g., from the earlier embodiments, and/or from the second embodiment) cannot be combined together, either in a single composition, or in a plurality of compositions, and utilized internally, such as in a subject, or in a subject in need thereof. Any combination of more than one active component described herein is contemplated in a composition, and a suitable or sufficient inhibitory activity (e.g., growth inhibition) will be found against the susceptible pathogens when the composition, formed as described herein, is internalized.

TABLE 3

| Active lauric acid derivative | MIC (mg/ml) S. epidermidis (chitosan prep. mixture at pH 5 or at pH 7) | MIC (mg/ml) E. coli (chitosan prep. mixture at pH 5 or at pH 7) | MIC (mg/ml) E. coli (chitosan prep. mixture at pH 9) |
|---|---|---|---|
| 12-(7-nitrobenzofurazan-4-ylamino) dodecanoic acid | 10 | — | — |
| 4-nitrophenyl dodecanoate | 10 | — | — |
| 1-lauroyl-rac-glycerol | 10 | — | — |
| 3-oxo-N-(2-oxocyclohexyl) dodecanamide | 10 | — | — |
| butyl laurate | 10 | — | — |
| benzyl laurate | 10 | — | — |
| isoamyl laurate | 10 | — | — |
| monolaurin | 10 | — | — |
| isopropyl laurate | 10 | — | — |
| pentyl laurate | 10 | — | — |
| hexyl laurate | 10 | — | — |
| octanoic acid | 10 | — | — |
| decanoic acid | 10 | — | — |

In a manner of manipulation in which a composition of a second embodiment is prepared, in a condition in which a preparatory mixture contains at least lecithin (with or without cholesterol), and a carrier or chitosan, and further includes a suitable additional active component (or one or more suitable additional active components), the preparatory mixture is acidic or neutral pH (e.g., about pH 5 and about pH 7, as examples, or between about pH 5 and about pH 7, as an example). As shown in TABLES 1, 2, 3, said compositions of the second embodiment demonstrated selective activity, with inhibitory activity against only susceptible representative Gram-positive bacterial strains, and exhibiting, in general, no inhibitory activity against tested representative Gram-negative bacterial strains. The selective nature associated with the compositions of the second embodiment was found regardless of whether synthesis of the composition (e.g., in the preparatory mixture for preparation of a composition of the second embodiment) was at an acidic, neutral, or alkaline pH. Without being bound by theory, it is believed that a lack of inhibitory activity against Gram-negative bacterial strains as exhibited in compositions of the second embodiment, those containing the one or more additional active components (see above), corresponds with the degree of hydrophobicity of these one or more additional active component (lauric acid, or the active lauric acid derivative). It is understood in the art that the degree of molecular hydrophobicity (or lipophilicity) is generally measured as a logarithmic value of the octanol-water partition coefficient P. The logarithmic value is referred to as log P.

Calculations for the log P value for the various representative active lauric acid derivatives described herein were made and are provided in TABLE 4, in which a lower log P values corresponds with an increased degree of molecular hydrophobicity.

TABLE 4

| Active lauric acid derivative | Number of carbon atoms in fatty acid backbone | Log P (hydrophobicity) |
|---|---|---|
| 12-aminododecanoic acid | 12 | 3.08 |
| 12-amino-1-dodecanoic acid methyl ester HCl | 12 | 3.54 |
| sucrose monolaurate | 12 | 2.12 |
| 12-(7-nitrobenzofurazan-4-ylamino) dodecanoic acid | 12 | 5.25 |
| 4-nitrophenyl dodecanoate | 12 | 6.8 |
| 1-lauroyl-rac-glycerol | 12 | 4.04 |
| butyl laurate | 12 | 7.09 |
| benzyl laurate | 12 | 7.24 |
| isoamyl laurate | 12 | 7.43 |
| monolaurin | 12 | 4.27 |
| isopropyl laurate | 12 | 6.37 |

TABLE 4-continued

| Active lauric acid derivative | Number of carbon atoms in fatty acid backbone | Log P (hydrophobicity) |
|---|---|---|
| pentyl laurate | 12 | 7.62 |
| hexyl laurate | 12 | 8.15 |
| octanoic acid | 8 | 2.9 |
| decanoic acid | 10 | 3.98 |

As depicted in TABLE 4, active lauric acid derivatives that could (and can) be manipulated as described above to shift from selective activity (in which inhibitory activity was against only susceptible Gram-positive bacteria) to broad-spectrum activity (in which inhibitory activity was against both susceptible Gram-positive and susceptible Gram-negative bacteria) are those that have the appropriate number of 12-carbon atoms in the fatty acid backbone, and are more highly hydrophobic, having a log P of less than 4. This is evidenced by finding that decanoic acid, having a log P of less than 4 but having 10 carbon atoms, was not found, when prepared as described herein into particulated or particle-containing compositions, to exhibit inhibitory activity against representative Gram-negative bacteria, even when manipulated to impart positivity (e.g., when prepared with the addition of a certain chemical agent that imparts a positive charge to the chitosan at neutral pH, or when prepared at a pH of 9). (See, TABLES 2 and 4). Similarly, octanoic acid, also having a log P of less than 4 and having only 8 carbon atoms, was also not found to exhibit inhibitory activity against representative Gram-negative bacteria, when prepared as described herein into particulated or particle-containing compositions, even when so prepared by manipulation to impart positivity (e.g., when prepared with the addition of a certain chemical agent that imparts a positive charge to the chitosan at neutral pH, or when prepared at a pH of 9). (See, TABLES 2 and 4).

For productive processing of any one or more active components, including one or more medium chain fatty acid as described herein (lauric acid) and/or one or more medium chain fatty acid derivatives as described herein, and for forming any of the compositions as described herein (compositions of the first embodiments and/or compositions of the second embodiments), a plurality of unexpected steps are required. This includes combining an active component (or more than one) with any one of lecithin, lecithin-like components (naturally occurring components), and/or with lecithin products or by-products (phosphatidylethanolamine (PE), phosphatidylinositol (PI), phosphatidic acid (PA), phosphatidylserine (PS), and lysophospholipids, e.g., lysophosphatidylethanolamine (LPE), sphingomyelin (SPM)), and/or bulky fatty acids, such as cholesterol, or lipids having a chain length predominantly from about C-14 to C-20). In some embodiments, the lecithin (or its variants thereof as described herein), may be further combined with at least one bulky fatty acid, such as cholesterol, or lipids having a chain length predominantly from about C-14 to C-20).

The lecithin (or variants thereof as just described, referred to hereinafter as lecithin) should be amphiphilic. The lecithin may include a mixture of naturally occurring phospholipids. The lecithin may include a mixture of naturally occurring phospholipids and/or glycerophospholipids (e.g., PC, PE, PI, and/or PA). In addition, or as an alternative, the lecithin may include bile salts. In addition, or as an alternative, the lecithin may include cholesterol. The lecithin (or variants thereof as just described) may be in any amount, often between about 0.001 wt. % and about 50 wt. %, based on the total wet weight of the composition. The lecithin may be in an amount between about 0.001 wt. % and about 20 wt. %, based on the total wet weight of the composition. The lecithin may be in an amount between about 0.001 wt. % and about 10 wt. %, based on the total wet weight of the composition. The lecithin may be in an amount between about 0.5 wt. % and about 20 wt. %, based on the total wet weight of the composition, or between about 1 wt. % and about 10 wt. %, based on the total wet weight of the composition, or between about 1 wt. % and about 20 wt. %, based on the total wet weight of the composition, or between about 5 wt. % and about 50 wt. %, based on the total wet weight of the composition, or between about 5 wt. % and about 20 wt. %, based on the total wet weight of the composition, or between about 10 wt. % and about 20 wt. %, based on the total wet weight of the composition, or between about 10 wt. % and about 30 wt. %, based on the total wet weight of the composition, or between about 5 wt. % and about 40 wt. %, based on the total wet weight of the composition. The lecithin may be predominantly phosphatidylcholine. The lecithin may include predominantly PC, with an additional phospholipid, lecithin, cholesterol, and/or bile or bile salts (often in a smaller amount). The lecithin may be from any source. The lecithin may be from a natural source, such as egg lecithin, soy lecithin. The lecithin may be in a granular form (e.g., L-alpha-lecithin granules).

In many embodiments, prior to the above combining step (with a sufficient amount of lecithin, or appropriate variants thereof), any one or more of the active components described herein (lauric acid and/or lauric acid derivatives, including any utilized for any of the first or second embodiments), either together (with some lecithin) or separately (without lecithin), should be initially suspended in an organic solvent, preferably an evaporatable organic solvent, such as chloroform, which, as a suspension, is then mixed with water, and further processed to evaporate the organic solvent. These prior steps are utilized to provide a more aqueous solution for the one or more of the lauric acid derivatives, which, in some embodiments, is a preferable state for the one or more lauric acid derivatives, prior to combining with the lecithin (or the sufficient lecithin variants thereof).

In some embodiments, the organic solvent of the prior step is buffered. In some embodiments, this organic solvent has a pH less than 7. In some embodiments, this organic solvent has a pH between about pH 4 and pH 7, or between pH 4 and pH 6. In some embodiments, this organic solvent is acidic and is between about pH 5 and pH 6, or between pH 4 and pH 5. In some embodiments, this organic solvent is or is between about pH 5 and pH 7. In some embodiments, the pH is above a physiologic pH (above pH 7).

The one or more of the active components (lauric acid and/or lauric acid derivatives, including any utilized for any of the first or second embodiments), when combining with lecithin, and/or when initially processing to provide in a more aqueous state, may be in a sufficient amount, generally between about 0.001 wt. % and about 50 wt. %, based on the total weight of the composition.

Generally, after combining any one or more of active components (hereinafter, any one or more of lauric acid and/or one or more lauric acid derivatives, including any utilized for any of the first or second embodiments) with lecithin in the manner(s) described above, the combination is provided in a preparatory mixture, when processed, may form particulates, liposomes, bilayer sheets, and/or micelles. Such forms may be sterilized. Particles, micelles, liposomes may generally occur via self-assembly once the preparatory mixture is prepared as described herein. The processing may include sonication. The processing may include freeze drying. In some embodiments, sonication may precede sterilization. In addition, or as an alternative, such processed forms may be filtered. Filtration may precede or follow sonication. Filtration may be performed at the same time as sterilization.

In some embodiments, the prepared (processed) forms (particulates, liposomes, bilayer sheets, and/or micelles) may be further coated in a coating step. When preparing, coating may be performed before, during, or after sonication. When preparing, coating may be performed before, during or after sterilization.

The coating may include coating or covering or otherwise applying (e.g., chemically, ionically, electrostatically, or otherwise) with a coating material. The coating material may be a non-toxic biopolymer or polysaccharide. The coating material may be a non-toxic biodegradable biopolymer, such as an aminopolysaccharide. The biopolymer or coating material may be a carrier. The coating material or carrier may be acidic, anionic, or modified with one or more carboxyl groups, phosphate groups, sulfur esters, or ester groups to interact or to selectively interact with one or more cell or cell types or target pathogens when introduced internally and/or topically. A suitable example of a coating material is chitosan or chitin. Chitosan may be hydroxylated. Additional examples include, but are not limited to, carrageenan, alginate, polylysine, xanthum gum, gellan gum, FucoPol, pullulan. In one or more embodiments, the coating step provides or involves an adhesion or incorporation of a portion of the coating material or carrier (e.g., biodegradable biopolymer or aminopolysaccharide) with the prepared form or with the particle. In some embodiments, the coating step may be performed by blending, dipping, spraying, and/or otherwise adding a prepared biodegradable biopolymer or aminopolysaccharide with the prepared form (e.g., particulates, liposomes, bilayer sheets, and/or micelles). The coating material may be provided in a suitable amount, or desired amount. The coating step may be followed by an incubation step. The incubation may include incubating for a few minutes, or one hour or more than one hour, or for several hours, or overnight. The coating step may include a suspension/dispersion/gelation/emulsion and/or a drying phase. Several coating steps may be performed in series, with the same or different coating materials. After coating, the coated composition(s) may be further agitated, sonicated, filtered, and/or sterilized.

Resulting compositions may, in final form, be particulated. The particles may have a large size distribution, or may be selected for a particular size. Generally, nanoparticle sizes are acceptable. Representative particle size examples include any size or range of sizes from 1 nm to 1000 nm, or any size or range of sizes therebetween. A higher diversity in nanoparticle size will generally be associated with larger variations in release of the one or more active components from the particles.

Representative and non-limiting examples are provided below.

Compositions containing a lauric acid derivative, 12-aminododecanoic acid or 12-amino-1-dodecanoic acid methyl ester, were prepared, and the preparations were performed independently (with either 12-aminododecanoic acid or 12-amino-1-dodecanoic acid methyl ester).

Initially, to determine basic characteristics, each active component was separately mixed, generally under agitated conditions, with water, and each was miscible with water. Each, after being mixed with water, was tested in a broth microdilution assay, against a variety of bacteria using amounts of the each of the lauric acid derivatives, ranging from about 0.0009 wt. % to about 8 wt. %. The bacteria included *Escherichia coli*, and *Staphylococcus aureus* (including MRSA strains). The minimum inhibitory concentration (MIC) needed to prevent growth of the target bacteria was evaluated based on a method published by Clinical Laboratory Standards Institute (CLSI), broth microdilution method M-07 (M07). In one or more embodiments, each active component (e.g., lauric acid derivative) as so prepared independently demonstrated no inhibitory activity against any of the bacteria tested, whether Gram-positive or Gram-negative. Each of the samples containing one of the lauric acid derivatives was compared with a positive control, decanoic acid. Decanoic acid, when prepared independently, was not miscible in water.

In another preparation, each of the lauric acid derivatives of TABLE 4 was independently suspended in an organic solvent, chloroform, and then mixed with water, generally under agitated conditions. This was followed by chloroform evaporation, generally under vacuum, using a freeze dryer. The same preparations were evaluated against the positive control, decanoic acid. Here, for all samples, the amount of water to the amount of chloroform was at least 2:1, and was as high as 10:1. The pH was neutral or was acidic. For each of the lauric acid derivatives as so prepared independently, there was no evidence of any growth inhibitory activity (growth inhibition) against representative bacteria tested in vitro, whether Gram-positive or Gram-negative. The positive control, decanoic acid, similarly prepared, also did not demonstrate growth inhibitory activity against representative bacteria when tested in vitro.

In a further preparation, lauric acid derivative, 12-aminododecanoic acid or 12-amino-1-dodecanoic acid methyl ester, was suspended individually (and independently) in an organic solvent, chloroform, and mixed with water, generally under agitated conditions. Here, for each sample, the amount of water to the amount of chloroform was at least 2:1, and was as high as 10:1. This was followed by chloroform evaporation, generally under vacuum using a freeze dryer. After removal of the chloroform, a lecithin solution was added to each sample. The lecithin was in a solution of acetic acid (e.g., 98 mM acetic acid and 2 mM sodium acetate), in which the amount of lecithin in solution was between about 1% to 5%. With addition of lecithin, each sample mixture contained up to about 4.8% lecithin (or generally about 5% or less), and up to about 7.8% of one of the lauric acid derivatives (or generally about 8% or less). pH of the solution was neutral. It is noted that the lecithin should be in a suitable form (e.g., solution or granules) acceptable for internal utilization (e.g., pharmaceutical grade). The lecithin may also include cholesterol, or other lecithin variants as described above, with similar results. Chitosan was then added to each of the samples, and each sample was then independently sonicated, followed by independent sterilization by high pressure filtration. The chitosan, as a coating, was generally mixed into the samples after addition of lecithin. The chitosan was added in several amounts up to about 10% (w/v). Chitosan was provided in solution (generally in the same solution provided with the lecithin, which was the solution of acetic acid, provided as 98 mM acetic acid and 2 mM sodium acetate). The mixing included stirring. With addition of chitosan, each sample mixture generally contained up to about 4.8% lecithin (or generally about 10% or less, or about 9% or less, or about 8% or less, or about 7% or less, or about 6% or less, or about 5% or less), up to about 5% chitosan (or generally about 10% or less, or about 9% or less, or about 8% or less, or about 7% or less, or about 6% or less, or about 5% or less), and up to about 7.8% of one of the lauric acid derivatives (or generally about 10% or less, or about 9% or less, or about 8% or less, or about 7% or less, or about 6% or less, or about 5% or less). Some sample mixtures contained about 0.75% chitosan (or between about 0.5% to about 1%, or any range or amount therebetween), about 1% lecithin (or between about 0.5% to about 2%, or any range or amount therebetween), and about 0.5% of one of the lauric acid derivatives (or between about 0.5% to about 1%, or any range or amount therebetween). Some mixtures were at a pH of between pH 5 and pH 7. Some mixtures were at a pH of about pH 9. After addition of chitosan, each of the samples was either simply filtered (e.g., via high pressure filtration for sterilization), or with 0.45 micrometer sterilized filter. In some embodiments, samples were sonicated, and thereafter underwent high pressure filtration for sterilization, or were filtered with 0.45 micrometer sterilized filter. Such samples just described, after filtration, or after sonication and filtration, were generally particulated, and may be reconstituted (and/or for dilution purposes), as necessary. Such samples may also be freeze dried. Said samples are also suitable for encapsulation. In some embodiments, sonication can decrease particle size, and also improve uniformity in size distribution (narrow the size distribution). In broth microdilution assays, each of the compositions, when formed as just described, exhibited growth inhibitory activity against representative Gram-positive pathogens and yeast, including the Gram-positive bacterial strains described and shown. The same preparation steps just described for the lauric acid derivatives samples were performed with the positive control, decanoic acid.

For TABLES 1 to 3, compositions were generally prepared as described above, and as further outlined in this paragraph. For these examples, the active component, as a lauric acid derivative or lauric acid, was suspended in an organic solvent, chloroform, and then mixed with water, under robust agitation. The amount of water to the amount of chloroform was at least about 2:1, and could be as high as 10:1. Chloroform was then evaporated (e.g., under vacuum using a freeze dryer). After removal of the chloroform, a 2.2% lecithin solution in an acetate buffer (e.g., 98 mM acetic acid and 2 mM sodium acetate) was prepared and added, so the final amount of the active component was about 1 part active component mixture and about 9 parts of the 2.2% lecithin solution. Of course, it is noted that other ranges to achieve final amount of the active component as described above (e.g., active component mixture and lecithin solution) may also be utilized. Cholesterol could also be optionally added. The mixture of lecithin and the active component was mixed and sonicated, and then a solution of about 1.5% chitosan was added. Thereafter, the entirety of the mixture containing the lecithin and the active component was further blended, in which a final ratio was about 1 part active component to about 9 parts of the 2.2% lecithin solution to about 10 parts of the 1.5% chitosan solution. The pH was then varied, to a pH of 5, or a pH of 7, or a pH of 9. In some mixtures having a pH of 7, a chemical agent imparting a positive charge to the chitosan was included in a form of glycol chitosan. In these tests, the chemical agent used was glycol. In these examples, the amount of chemical agent, glycol was about one molecule glycol moiety to one molecule chitosan sacharide unit; higher amounts of glycol moieties are also acceptable, while lower amounts of glycol moieties were often found to decrease overall inhibitory activity associated with a composition when formed and tested in vitro. It is noted that negatively charged chitosan containing particles were prepared. The negatively charged chitosan containing particles exhibited no inhibitory activity. After mixing, the mixtures could each be filtered through a 0.45 microMol filter. In some tests, the mixtures were sonicated before filtering. Sonication produced small particles. In some studies, particles were freeze dried as a powder (generally, after mixing, sonicating and filtering). In such freeze-dried preparation, all compositions were found to retain their activity. This shows that particles may be stored, and/or encapsulated, any of which should have a long shelf-life.

The positive controls were prepared and evaluated in a similar manner. All prepared samples were tested using a broth microdilution test.

Without being bound by theory, the charge of the chitosan or carrier material on compositions described herein appears to influence the type of action exhibited by certain chitosan- or carrier-containing particles described herein. For example, synthesis of chitosan- or carrier-containing particles at a neutral pH (e.g., pH 7) in the manner described herein appears to improve the degree of activity of the lauric acid derivatives against Gram-positive pathogens, such that inhibitory activity or growth inhibition is stronger in the compositions described herein, particularly when the active component when used alone (and not in a composition as described herein) exhibited some but only very weak activity against certain Gram-positive pathogens. When the chitosan- or carrier-containing particle includes an active component that has a higher hydrophobicity (having log P value less than 4), then there is both a stronger inhibitory activity as well as broad spectrum activity against both Gram-positive pathogens (e.g., Gram-positive pathogens described herein) and Gram-negative pathogens (e.g., Gram-negative pathogens described herein) when the chitosan- or carrier-containing particles are synthesized in a hydroxyl-dominated environment (e.g., when synthesis occurs at pH 9, or when synthesis occurs at pH 7 or pH 9 and the chitosan or carrier material is a positively charged chitosan or carrier material). This also occurs when the chitosan- or carrier-containing particle includes an active component that has a log P value that is less than 4 and includes a methyl and/or ethyl side chain (e.g., 12-amino-1-dodecanoic acid methyl ester). It is noted that synthesis of negatively charged chitosan- or carrier-containing particles showed no activity against Gram-positive or Gram-negative pathogens. Examples of active components that have a log P value less than 4 include 12-aminododecanoic acid, 12-amino-1-dodecanoic acid methyl ester, and sucrose monolaurate. For sucrose monolaurate, the stronger inhibitory activity as well as broad spectrum activity against both Gram-positive pathogens and Gram-negative pathogens was observed in vitro at least when a hydroxyl dominated environment was created by performing the synthesis (with chitosan) at pH 9. For 12-aminododecanoic acid, 12-amino-1-dodecanoic acid methyl ester, and sucrose monolaurate, the stronger inhibitory activity as well as broad spectrum activity against both Gram-positive pathogens and Gram-negative pathogens, was observed in vitro at least when a hydroxyl dominated environment was created by performing the synthesis (with chitosan) at pH 7 and by utilizing a positively charged chitosan in the synthesis. Having an active component with a log P value less than 4, (or less than 3), will, thereby, influence activity characteristics of a composition or formulation prepared therefrom, and will allow, under different synthesis environments, as just described, the capability of creating a selective or a broad-spectrum antimicrobial agent.

The broad spectrum activity of a composition described herein is exemplified in TABLE 5, in which the active component, sucrose monolaurate, being hydrophobic and having a log P value less than 4, was prepared in a manner described above, which included synthesis of chitosan-containing particles by initially blending about 1 part sucrose monolaurate with about 9 parts 2.2% lecithin solution in an acetate buffer, mixing and sonicating, and then adding about 1.5% chitosan in an acetate buffer, such that a final ratio is about 1 part sucrose monolaurate to about 9 parts of 2.2% lecithin solution to about 10 parts of 1.5% chitosan solution. With the chitosan solution, the mixture is in a buffered solution that is at pH 9. After the chitosan is added, the mixture is blended, sonicated and filtered through a sterile filter. Samples, in a particulated form, and up to 10 mg/ml were evaluated for inhibitory activity against Gram-positive and Gram-negative pathogens, including antibiotic-resistant pathogens. The antibiotic-resistant strains tested included at least twelve of the antibiotic-resistant bacteria identified by the WHO Global Priority List as being of concern, and three of the tested strains being those considered to be of critical concern (Priority 1). Representative findings are provided in TABLE 5, depicting the pathogens tested with a composition comprising the active component, sucrose monolaurate, prepared at pH 9 in order to harness the broad-spectrum activity of the active component.

TABLE 5

| Pathogen | Growth inhibition (chitosan prep. mixture at pH 9) |
|---|---|
| *Acinetobacter baumannii*, carbapenem-resistant | + |
| *Pseudomonas aeruginosa*, carbapenem-resistant | + |
| Enterobacteriaceae, carbapenem-resistant, cephalosporin-resistant | + |
| *Staphylococcus aureus*, methicillin-resistant, vancomycin resistant | + |
| *Campylobacter*, fluoroquinolone-resistant | + |
| *Salmonella* spp., fluoroquinolone-resistant | + |
| *Streptococcus pneumoniae* | + |
| *Shigella* spp., fluoroquinolone-resistant | + |
| *Chlostridium difficile* | + |
| *Candida* | + |
| *Mycobacterium* spp. | + |
| Group A *Streptococcus* | + |
| Group B *Streptococcus* | + |

Laboratory trials have shown that no resistance has developed in pathogens exposed to the compositions described herein, even with long term, repeated exposure (data not shown). In addition, no intrinsic resistance can or has been detected in target pathogens. Animal trials show no safety concerns, in which various groups of 10 mice are given a set of capsules, orally, three times per day and continued for seven days, each of the set of capsules containing approximately 4 mg of one of the active components, either 12-amino-1-dodecanoic acid methyl ester, or sucrose monolaurate (independently), and each of the active components in the chitosan-containing particles prepared generally as described herein. A placebo group is also included, in which a group of 10 mice are given a placebo set of capsules, orally, three times per day and continued for seven days, each of the placebo set of capsules containing similarly prepared chitosan-containing particles without an active component, the preparation being generally as described herein. Initial mice have been infected with *Salmonella typhimurium* prior to oral delivery of one of the set of capsules. The capsules may be vegetable capsules. The capsules may have an enteric coating. For delivery, a formulation may be prepared in a manner understood in the relevant art. For delivery, a formulation may be in at least any one or more of the following forms: liquid, capsule, dried powder, mist, and the like. For delivery, the formulation will contain pharmaceutical grade materials, including one or more excipients and or fillers for internal and/or topical delivery in sufficient amounts known to those of skill in the relevant art. Flavors, colors, sugars, sugar-substitutes, and the like may also be included in any of the formulations, as is understood to those of skill in the relevant art.

Active components of the compositions described herein are associated with a strong safety profile. Active components of the compositions described herein have GRAS status in the U.S.

The above description and examples demonstrate unexpectedly that the described active components (one or more of lauric acid, and lauric acid derivatives), prepared in the unexpected and/or nonobvious manner, as described above, may be so prepared to alter the level of action and/or scope of activity of a final composition. As such, a composition may be manipulated to achieve a different level of activity and/or a more selective or expansive inhibitory action. This allows fine tuning where needed in the treatment of one or more pathogens. At least some of the composition described herein are capable of providing bacteriostatic against gram-positive bacteria, as well as gram-negative bacteria. The broad spectrum inhibitory activity found as described herein would not have been anticipated, particularly in view of the conflicting and contradictory reports that pre-date these findings. The inhibitory activity found with the active components described herein appear to differ from previous understandings of lauric acid.

By utilizing preparations described herein, formulations containing the lauric acid and/or any one or more of the lauric acid derivatives may be prepared as described herein, at desired dosing concentrations and/or for desired inhibitory activity, and, when necessary, with the appropriate fillers and/or additives (e.g., excipient, colorant, flavorant, etc.) known to the skilled artisan (e.g., to provide a formulation in the form of any one or more of a liquid, gel, suspension, tablet, caplet, capsule, granules, powder, inhalant, lozenge, mouthwash, cream, lotion, and the like). Such formulations may now be internalized, which has not been previously shown. Dosing of any of the formulations may be maximized based on pharmacokinetic and/or pharmacodynamics data, which can be obtained by known methods known already in the relevant art.

In addition, any of said compositions described herein may still be deliverable topically. Thus, formulations, when properly prepared in the manner described herein and with further preparation dependent on the form of deliver (and in a manner known to the skilled artisan in the relevant art), may be administered for delivery internally and/or externally, and may be further tailored for inhibiting growth (bacteriostatic activity) and/or killing (bactericidal activity) of one or more susceptible pathogens. The nature of the lauric acid and lauric acid derivatives prepared as described herein makes them suitable for many uses. The lauric acid derivatives described herein are likely active at inhibiting growth and/or killing yeast, as well as fungi. One or more lauric acid derivatives described herein are active against select Gram-positive bacteria or yeast. One or more lauric acid derivatives may be provided at sub-inhibitory amounts for bacteriostatic activity. One or more lauric acid derivatives may be provided serially at sub-inhibitory amounts for bacteriostatic activity. Higher and lower doses can also be administered with greater or lesser efficacy. Formulations of the described compositions can be administered for internal and/or external activity at or around a pathogen MIC for anti-inflammatory activity. Formulations of the described compositions can be administered for internal and/or external activity below the pathogen MIC for anti-inflammatory activity with or without serial exposures to reduce resistance development (or change in MIC). Formulations of the described compositions can also be administered outside the pathogen MIC range and still provide anti-inflammatory activity.

Although representative processes and compositions have been described in detail herein, those skilled in the art will recognize that various substitutions and modifications for preparation of the new lauric acid derivatives may be made without departing from the scope and spirit of what is described and defined by the appended claims.

What is claimed is:

1. A composition for growth-inhibitory action against at least one susceptible pathogen, the composition comprising:
   at least one of a lauric acid derivative as an active component of the composition, the lauric acid derivative selected from at least one of 12-aminododecanoic acid, 12-amino-1-dodecanoic acid methyl ester, and sucrose monolaurate, each lauric acid derivative exhibiting hydrophobicity and a partition coefficient, P, in which a logP value of each lauric acid derivative is less than 4;
   lecithin; and
   glycol chitosan,
   wherein the composition includes particulates, the particulates comprising at least the active component, the glycol chitosan and the lecithin, and wherein the glycol chitosan is on an outer portion of at least a portion of the particulates,
   wherein the composition is suitable for utilization in a formulation, the formulation suitable for internal delivery, and
   wherein, in the presence of the at least one susceptible pathogen, the composition is a direct-acting composition inhibiting growth of the at least one susceptible pathogen, and the at least one susceptible pathogen is a Gram-negative bacteria.

2. The composition of claim 1, wherein the lauric acid derivative is in an amount between about 0.001 wt. % and 30 wt. % of the composition.

3. The composition of claim 1, wherein the lecithin is in an amount up to about 10 wt. % of the composition based on the weight of the composition.

4. The composition of claim 1, wherein the lecithin is in an amount up to about 30 wt. % of the composition, and wherein the lecithin is any one or more of the lecithin alone, the lecithin with naturally occurring phospholipid, the lecithin with naturally occurring glycerophospholipid, and the lecithin with the naturally occurring phospholipid and the naturally occurring glycerophospholipid, and
   wherein the naturally occurring phospholipid is selected from the group consisting of phosphatidylcholine, phosphatidylethanolamine, phosphatidylinositol, phosphatidic acid, phosphatidylserine, lysophospholipid, lyso-phosphatidylethanolamine, sphingomyelin, and various combinations thereof.

5. The composition of claim 1, wherein the glycol chitosan is in an amount up to about 10 wt. % of the composition, based on the weight of the composition.

6. The composition of claim 1, wherein the composition utilized in the formulation comprises particles, and further comprises a sufficient amount of one or more excipients forming the formulation.

7. The composition of claim 1, wherein the composition is a suspension comprising particles.

8. The composition of claim 1, wherein the composition is in a dry or powder form.

9. The composition of claim 1, wherein prior to utilization in the formulation the particulates are any one or more of sonicated and filtered.

10. A method of making a composition, the composition having growth-inhibitory action against a susceptible pathogen that is at least one Gram-negative bacteria, the method comprising:
    suspending at least one of a lauric acid derivative with chloroform to form a suspension, the lauric acid derivative being an active component of the composition, and selected from at least one of 12-aminododecanoic acid, 12-amino-1-dodecanoic acid methyl ester, and sucrose monolaurate, wherein each lauric acid derivative exhibits hydrophobicity and a partition coefficient, P, in which a logP value of each lauric acid derivative is less than 4;
    mixing the suspension with water;
    combining the suspension with a lecithin to form a mixture, the lecithin being in an acidic or neutral solution;
    combining the suspension containing the lecithin with a glycol chitosan, the glycol chitosan being in a same acidic or neutral solution used for the lecithin; and
    sonicating and then filtering the suspension, thereby providing a composition containing particulates,
    wherein the composition containing particulates comprises at least the active component, the glycol chitosan and the lecithin, and wherein the glycol chitosan is on at an outer portion of at least a portion of the particulates, and
    wherein the composition is for use against the at least one Gram-negative bacteria, and is suitable for use in a formulation, the formulation being for utilization internally.

11. The method of claim 10, wherein mixing the suspension with water includes sonicating the suspension with water.

12. The method of claim 10, wherein the lecithin in the acidic or neutral solution is sonicated before the step of combining to form the mixture.

13. A particle-containing composition for growth-inhibitory action against at least one susceptible pathogen, the at least one susceptible pathogen being a susceptible Gram-negative bacteria, the particle-containing composition comprising lecithin, the lecithin forming at least a portion of the particle-containing composition, the particle-containing composition further comprising:
    an active component being one of a fatty acid derivative of lauric acid or an esterified fatty acid derivative of lauric acid, thereby having a 12-carbon atom backbone, and the active component on its own exhibiting hydrophobicity and,
    wherein the particle-containing composition has at least one further characteristic comprising glycol chitosan on at least an outer portion of particles of the composition; and
    wherein the particle-containing composition is for use against the susceptible Gram-negative bacteria as a direct-acting composition on the susceptible Gram-negative bacteria for inhibiting growth of the susceptible Gram-negative bacteria.

14. The particle-containing composition of claim 13, wherein the lecithin is any one or more of the lecithin alone, the lecithin with naturally occurring phospholipid, the lecithin with naturally occurring glycerophospholipid, and the lecithin with naturally occurring phospholipid and the naturally occurring glycerophospholipid,
wherein the naturally occurring phospholipid is selected from the group consisting of phosphatidylcholine, phosphatidylethanolamine, phosphatidylinositol, phosphatidic acid, phosphatidylserine, lysophospholipid, lyso-phosphatidylethanolamine, sphingomyelin, and various combinations thereof.

15. The particle-containing composition of claim 13, wherein the particle-containing composition is formulated as an antimicrobial, and, as the antimicrobial, exhibits growth inhibitory activity against the susceptible Gram-negative bacteria.

16. The particle-containing composition of claim 13, wherein the susceptible Gram-negative bacteria includes one or more from the group consisting of *Escherichia coli, Acinetobacter baumannii, Pseudomonas aeruginosa, Campylobacter* spp., *Salmonella* spp., and *Shigella* spp.

17. The particle-containing composition of claim 13, wherein the susceptible Gram-negative bacteria is resistant to one or more antibiotics.

18. The particle-containing composition of claim 13, wherein the active component is selected from one or more of the group consisting of 12-aminododecanoic acid, 12-amino-l-dodecanoic acid methyl ester, and sucrose monolaurate.

19. The particle-containing composition of claim 13, wherein the active component is selected from one or more of the group consisting of 12-(7-nitrobenzofurazan-4-ylamino) dodecanoic acid, 4-nitrophenyl dodecanoate, 3-oxo-N-(2-oxocyclohexyl) dodecanamide, butyl laurate, benzyl laurate, isoamyl laurate, monolaurin, isopropyl laurate, pentyl laurate, and hexyl laurate.

20. The particle-containing composition of claim 13, wherein the at least one susceptible pathogen further comprises a Gram-positive bacterium selected from one or more from the group consisting of *Staphylococcus aureus, Staphylococcus epidermidis, Streptococcus pneumoniae, Chlostridium difficile, Mycobacterium* spp., Group A *Streptococcus*, and Group B *Streptococcus*.

* * * * *